(12) United States Patent
Brockway et al.

(10) Patent No.: US 9,050,007 B1
(45) Date of Patent: *Jun. 9, 2015

(54) EXTRACTION OF CARDIAC SIGNAL DATA

(71) Applicant: VivaQuant LLC, St. Paul, MN (US)

(72) Inventors: Marina Brockway, St. Paul, MN (US);
Brian Brockway, St. Paul, MN (US)

(73) Assignee: VivaQuant LLC, St. Paul, MN (US)

( * ) Notice: Subject to any disclaimer, the term of this patent is extended or adjusted under 35 U.S.C. 154(b) by 72 days.

This patent is subject to a terminal disclaimer.

(21) Appl. No.: 13/872,774

(22) Filed: Apr. 29, 2013

Related U.S. Application Data

(63) Continuation of application No. 13/172,415, filed on Jun. 29, 2011, now Pat. No. 8,433,395, and a continuation-in-part of application No. 12/938,995, filed on Nov. 3, 2010, now Pat. No. 8,632,465.

(60) Provisional application No. 61/359,462, filed on Jun. 29, 2010, provisional application No. 61/370,026, filed on Aug. 2, 2010, provisional application No. 61/257,718, filed on Nov. 3, 2009, provisional application No. 61/366,052, filed on Jul. 20, 2010.

(51) Int. Cl.
*A61B 5/00* (2006.01)
*A61B 5/04* (2006.01)
*A61B 5/0452* (2006.01)

(52) U.S. Cl.
CPC ........... *A61B 5/04012* (2013.01); *A61B 5/0452* (2013.01)

(58) Field of Classification Search
CPC ....................................... A61B 5/0452–5/0472
USPC ................................................... 600/508–523
See application file for complete search history.

(56) References Cited

U.S. PATENT DOCUMENTS

| | | | |
|---|---|---|---|
| 5,090,418 | A | 2/1992 | Squires et al. |
| 5,521,851 | A | 5/1996 | Wei et al. |
| 5,792,065 | A | 8/1998 | Xue et al. |
| 5,817,027 | A | 10/1998 | Arand et al. |
| 5,827,195 | A | 10/1998 | Lander |
| 5,987,352 | A | 11/1999 | Klein et al. |
| 6,389,308 | B1 | 5/2002 | Shusterman |
| 6,589,189 | B2 | 7/2003 | Meyerson et al. |
| 6,690,959 | B2 | 2/2004 | Thompson |

(Continued)

FOREIGN PATENT DOCUMENTS

WO  2013/043157 A2  3/2013

OTHER PUBLICATIONS

B. Widrow, et al., "Adaptive noise cancelling: principles and applications," IEEE Proc., vol. 63, No. 12, pp. 1692-1716, Dec. 1975.

(Continued)

*Primary Examiner* — Scott Getzow
(74) *Attorney, Agent, or Firm* — Crawford Maunu PLLC

(57) ABSTRACT

A T-wave offset point of an ECG signal is provided. In accordance with various example embodiments, a location of a QRS complex in the ECG signal is identified and used to determine a first time window of the ECG signal in which to search for a T-wave offset point. The T-wave offset point is identified within the first time window, and the identified T-wave offset point is provided as an output based upon a noise characteristic of the ECG signal in a second time window that includes at least a portion of the T-wave.

36 Claims, 17 Drawing Sheets

(56) References Cited

U.S. PATENT DOCUMENTS

| | | | |
|---|---|---|---|
| 6,701,170 | B2 | 3/2004 | Stetson |
| 6,822,564 | B2 | 11/2004 | Al-Ali |
| 7,096,060 | B2 | 8/2006 | Arand et al. |
| 7,115,096 | B2 | 10/2006 | Siejko et al. |
| 7,236,819 | B2 | 6/2007 | Brockway et al. |
| 7,272,265 | B2 | 9/2007 | Kouri et al. |
| 7,376,453 | B1 | 5/2008 | Diab et al. |
| 7,627,369 | B2 | 12/2009 | Hunt |
| 7,672,717 | B1 | 3/2010 | Zikov et al. |
| 7,840,259 | B2 | 11/2010 | Xue et al. |
| 8,086,304 | B2 | 12/2011 | Brockway et al. |
| 8,201,330 | B1 | 6/2012 | Rood et al. |
| 8,214,007 | B2 | 7/2012 | Baker et al. |
| 8,271,073 | B2 | 9/2012 | Zhang et al. |
| 8,348,852 | B2 | 1/2013 | Bauer et al. |
| 8,460,189 | B2 | 6/2013 | Libbus et al. |
| 8,478,389 | B1 | 7/2013 | Brockway et al. |
| 2005/0010120 | A1 | 1/2005 | Jung et al. |
| 2005/0234361 | A1 | 10/2005 | Holland |
| 2005/0283090 | A1 | 12/2005 | Wells |
| 2007/0219453 | A1 | 9/2007 | Kremliovsky et al. |
| 2007/0219455 | A1 | 9/2007 | Wong et al. |
| 2007/0260151 | A1 | 11/2007 | Clifford |
| 2007/0265508 | A1 | 11/2007 | Sheikhzadeh-Nadjar |
| 2008/0065158 | A1 | 3/2008 | Ben-Ezra et al. |
| 2008/0097537 | A1 | 4/2008 | Duann et al. |
| 2008/0183093 | A1 | 7/2008 | Duann et al. |
| 2008/0200832 | A1 | 8/2008 | Stone |
| 2009/0069703 | A1 | 3/2009 | Takla et al. |
| 2009/0222262 | A1 | 9/2009 | Kim et al. |
| 2012/0165691 | A1 | 6/2012 | Ting et al. |
| 2012/0197144 | A1 | 8/2012 | Christ et al. |
| 2012/0232417 | A1 | 9/2012 | Zhang |
| 2013/0109937 | A1 | 5/2013 | Banet et al. |
| 2014/0005988 | A1 | 1/2014 | Brockway |

OTHER PUBLICATIONS

H. Boudoulas, YH. Sohn, W. O'Neill, R. Brown, AM. Weissler. The QT greater that QS2 syndrome: a new mortality risk indicator in coronary artery disease. American Journal of Cardiology, vol. 50 (6) pp. 1229-1235 (1982).

G. Moody, W. Muldrow, and R. Mark, "A noise stress test for arrhythmia detectors," Computers in Cardiology, pp. 381-384 (1984).

K. R. Rao and P. Yip, "Discrete Cosine Transform: Algorithms, Advantages, Applications," San Diego, CA: Academic (1990).

J. Woods. Subband Coding, Kluwer Academic Press (1990).

K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).

NV Thakor and YS Zhu, "Applications of adaptive filtering to ECG analysis: noise cancellation," IEEE Transactions on Biomedical Engineering, vol. 38, No. 8, pp. 785-794 (Aug. 1991).

S. Mallat and W. L.-Hwang, "Singularity Detection and Processing with Wavelets," IEEE Transactions on Information Technology (38), pp. 617-643 (1992).

S. Mallat and S. Zhong, "Characterization of Signals from Multiscale Edges," IEEE Trans. Pattern Anal. Mach. Intell. 14, 7 (Jul. 1992).

Vaidyanathan, Multirate Systems and Filter Banks, Prentice Hall, 1993.

Y. Pati, R. Rezaiifar and P. Krishnaprasad, "Orthogonal Matching Pursuit: Recursive Function Approximation With Applications to Wavelet Decomposition," in Asilomar Conference on Signals, Systems and Computers, vol. 1, pp. 40-44 (Nov. 1993).

S. Mallat and Z. Zhang, "Matching Pursuits with Time-Frequency Dictionaries," IEEE TSP(41), No. 12, pp. 3397-3415 (Dec. 1993).

P. Comon, "Independent component analysis, a new concept?," Signal Process. Special Issue on Higher Order Statistics, vol. 36, No. 3, pp. 287-314 (Apr. 1994).

Donoho, D.L., I.M. Johnstone (1994), "Ideal spatial adaptation by wavelet shrinkage," Biometrika, vol. 81, pp. 425-455.

Y. Xu, J. Weaver, D. Healy, Jr. and J. Lu, "Wavelet Transform Domain Filters: A Spatially Selective Noise Filtration Technique," IEEE Transactions on Image Processing, vol. 3, No. 6, pp. 747-758 (1994).

D. L. Donoho, "Denoising by Soft-Thresholding," IEEE Trans. on Inf. Theory, vol. 41, No. 3, pp. 613-627 (May 1995).

A.Bell and T. Sejnowski, "An Information-Maximization Approach to Blind Separation and Blind Deconvolution," Neural Computation, 7:1129-1159. (1995).

M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).

V. Afonso, W. Tompkins, T. Nguyen, K. Michler and S. Luo, "Comparing Stress ECG Enhancement Algorithms," IEEE Engineering in Medicine and Biology, pp. 37-44 (May/Jun. 1996).

J._Francois Cardoso, "Infomax and Maximum Likelihood for Source Separation," IEEE Letters on Signal Processing, vol. 4, No. 4, pp. 112-114 (Apr. 1997).

M. L. Hilton, "Wavelet and Wavelet Packets Compression of Electrocardiogram," IEEE Transactions on Biomedical Engineering, vol. 44, No. 5, pp. 394-402 (May 1997).

A. Hyvärinen "New Approximations of Differential Entropy for Independent Component Analysis and Projection Pursuit," In Advances in Neural Information Processing Systems, vol. 10, pp. 273-279, MIT Press. (1997).

W. Sweldens. The lifting scheme: A construction of second generation wavelets. SIAM J. Math. Anal., 29(2):511-546, 1997.

American National Standard ANSI/AAMI EC57:1998, Testing and Reporting Performance Results of Cardiac Rhythm and ST Segment Measurement Algorithms.

Testing and reporting performance results of cardiac rhythm and ST-segment measurement algorithms ANSI/AAMI EC57:1998.

L. Torres-Pereira, et. al. "A Biotelemetric Heart Sound Monitoring System," in Proceedings of the 14th International Symposium on Biotelemetry. Marburg, 1998.

A. Hyvärinen, "Fast and Robust Fixed-Point Algorithms for Independent Component Analysis," IEEE Transactions on Neural Networks, vol. 10, No. 3, pp. 626-634 (May 1999).

J.-F. Cardoso, "High-Order Contrasts for Independent Component Analysis," Neural Comput., vol. 11, No. 1, pp. 157-192 (1999).

S. Chen, D Donoho, and M. Saunders, "Atomic Decomposition by Basis Pursuit," SIAM J. Scientific Computing, vol. 20, No. 1, pp. 33-61 (1999).

Q. Pan, L. Zhang, G. Dai and H. Zhang, "Two Denoising Methods by Wavelet Transform," IEEE Trans. on SP, vol. 47, No. 12, pp. 3401-3406 (Dec. 1999).

G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).

S. Mallat, "A Wavelet Tour of Signal Processing," Academic Press, 1999.

Langley, P.; Di Bernardo, D.; Murray, A.; Comparison of three measures of QT dispersion. Computers in Cardiology 1999 pp. 69-72.

Goldberger AL et al. PhysioBank, PhysioToolkit, and PhysioNet: components of a new research resource for complex physiologic signals. Circulation 101(23): e215-e220, 2000 (Jun. 13).

Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).

M. Marcellin, M. gormish, A. Bilgin and M. Boleik, "An Overview of JPEG-2000," Proc. of IEEE Data Compression Conference, pp. 523-541 (2000).

L. K. Saul and J. B. Allen, "Periodic component analysis: An eigenvalue method for representing periodic structure in speech," in NIPS, [Online]., pp. 807-813 (2000). Available: http://www.cs.cmu.edu/Groups/NIPS/00papers-pub-on-web/SaulAllen.pdf.

(56) References Cited

OTHER PUBLICATIONS

C. Taswell, "The What, How, and Why of Wavelet Shrinkage Denoising," Computing in Science and Engineering, vol. 2, No. 3, pp. 12-19 (2000).

J. S. Richman and J. R. Moorman, Physiological time-series analysis using approximate entropy and sample entropy Am. J. Physiol. 278, H2039 (2000).

K. Sayood, "Introduction to Data Compression," Academic Press 2000.

Malik M, Batchvarov VN. Measurement, interpretation and clinical potential of QT dispersion. J Am Coll Cardiol. Nov. 15, 2000;36(6):1749-66.

A. Hyvärinen and E. Oja, "Independent Component Analysis: Algorithms and Applications," Neural Networks, 13(4-5), pp. 411-430 (2000).

R. Mayerburg. Sudden cardiac death: exploring the limits of our knowledge. Journal of Cardiovascular Electrophysiology, vol. 12, No. 3, Mar. 2001.

M. Brennan, M. Palaniswami, and P. Kamen. Do Existing Measures of Poincaré Plot Geometry Reflect Nonlinear Features of Heart Rate Variability? IEEE Transactions on Biomedical Engineering, vol. 48, No. 11, Nov. 2001.

D. Donoho and X. Huo, "Uncertainty Principles and Ideal Atomic Decomposition," IEEE Transactions on Information Theory, vol. 47, No. 7, pp. 2845-2862 (Nov. 2001).

M. Zibulevsky and B. Pearlmutter, "Blind Source Separation by Sparse Decomposition in a Signal Dictionary," Neural Computation. vol. 13, pp. 863-882 (2001).

Oweiss, K.G. Anderson, D.J. "MASSIT—Multiresolution Analysis of Signal Subspace Invariance Technique: a novel algorithm for blind source separation", Conference on Signals, Systems and Computers Publication Date: 2001 vol. 1, pp. 819-823 vol. 1.

M. Costa, A. L. Goldberger, and C.-K. Peng, Multiscale Entropy Analysis of Complex Physiologic Time Series, Phys. Rev. Lett. 89, 6, (2002).

B. U. Kohler, C. Hennig, R. Orglmeister. The principles of software QRS detection. IEEE Engineering in Medicine and Biology Magazine, vol. 21, No. 1. (2002), pp. 42-57.

Tsalaile, et al. "Blind Source Extraction of Heart Sound Signals From Lung Sound Recordings Exploiting Periodicity of the Heart Sound," ICASSP 2008 IEEE, p. 461-464.

Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.

Kellermann, et al.,"A mobile phone based alarm system for supervising vital parameters in free moving rats," BMC Research Notes 2012, 5:119, Feb. 23, 2012.

http://www.simplehelp. net/2006/09/12/how-to-set-up-outlook-2003-for-email/.

G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).

T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).

D A Clunie, "Extension of an open source DICOM toolkit to support SCP-ECG waveforms," 2nd OpenECG Workshop 2004, Berlin, Germany.

J.-P Martinez, et. al., "A wavelet-based ECG delineator: Evaluation on standard databases," IEEE transactions on biomedical engineering, vol. 51, No. 4, pp. 57 (2004).

Thomsen, M. B., Verduyn, S. C., Stengl, M., Beekman, J. D., de Pater, G., van Opstal, J., et al. (2004). Increased short-term variability of repolarization predicts d-sotalolinduced torsade de pointes in dogs. Circulation, 110, 2453-2459.

Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.

Madalena Costa.et. al. Multiscale entropy analysis of biological signals. Physical Review E 71, 021906 s2005d, (2005).

M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).

S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).

Hamlin RL. Non-drug-related electrocardiographic features in animal models in safety pharmacology. J Pharmacol Toxicol Methods. Jul.-Aug. 2005; 52(1): 60-76.

HJ van der Linde, A van Water, W Loots, B van Dueren, K van Ammel, M Peters and DJ Gallacher. A new method to calculate the beat-to-beat instability of QT duration in drug-induced long QT in anesthetized dogs. Journal of Pharmacological and Toxicological Methods 52 (2005) 168-177.

R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).

M. Blanco-Velasco, B. Weng and KE Barner, "A New ECG Enhancement Algorithm for Stress ECG Tests," Computers in Cardiology, vol. 33, pp. 917-920 (2006).

Chen PC, Lee S, Kuo CD. Delineation of T-wave in ECG by wavelet transform using multiscale differential operator. IEEE Trans Biomed Eng. Jul. 2006;53(7):1429-33.

K. Zhang, L.-W. Chan, "An Adaptive Method for Subband Decomposition ICA", Neural Computation, vol. 18, No. 1, pp. 191-223 (2006).

R. Brychta, "Wavelet analysis of autonomic and cardiovascular signals," PhD Dissertation. Vanderbilt University (Aug. 2006).

M. Aminghafari, N. Cheze, J.-M Poggi, "Multivariate de-noising using wavelets and principal component analysis," Computational Statistics & Data Analysis, 50, pp. 2381-2398 (2006).

Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).

Chouakri S.A., et al. ECG signal smoothing based on combining wavelet denoising levels. Asian Journal of Information Technology. vol. 5, pp. 667-677. 2006.

Inan, O.T.; Giovangrandi, L.; Kovacs, G.T.A.; Robust Neural-Network-Based Classification of Premature Ventricular Contractions Using Wavelet Transform and Timing Interval Features , IEEE Transactions on Biomedical Engineering vol. 53 , Issue: 12 , , pp. 2507-2515, (2014).

L. Smith, A tutorial on Principal Components Analysis, (2014).

Akinori Ueno, et al. Capacitive sensing of electrocardiographic potential through cloth from the dorsal surface of the body in a supine position: a preliminary study. IEEE Transactions on Biomedical Engineering, vol. 54, No. 4, Apr. 2007, pp. 759-766.

K. Oweiss , A. Mason , Y. Suhail , A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).

K. Todros and J. Tabrikian, "Blind Separation of Independent Sources Using Gaussian Mixture Model," IEEE Transactions on Signal Processing, vol. 55, No. 7, pp. 3645-3658 (Jul. 2007).

R. Sameni, M. Shamsollahi, C. Jutten and G. Glifford, "A Nonlinear Bayesian Filtering Framework for ECG Denoising," IEEE Transactions on Biomedical Engineering , vol. 54, No. 12, pp. 2172-2185 (2007).

X. Li, X. Yao, J. Fox, and J. Jefferys, "Interaction Dynamics of Neuronal Oscillations Analysed Using Wavelet Transforms," Journal of Neuroscience Methods 160, pp. 178-185 (2007).

R Schimpf, Ch Antzelevitch, D Haghi, C Giustetto, A Pizzuti, F Gaita, Ch Veltmann, Ch Wolpert and M Borggrefe. Electromechanical coupling in patients with the short QT syndrome: Further insights into the mechanoelectrical hypothesis of the U wave. Heart Rhythm. Feb. 2008 ; 5(2): 241-245.

(56) References Cited

OTHER PUBLICATIONS

Sarkar S, Ritscher D, Mehra R. A detector for a chronic implantable atrial tachyarrhythmia monitor. IEEE Trans Biomed Eng. Mar. 2008;55(3):1219-24.

M. Malik, K. Hnatkova, T. Novotny, G Schmidt Subject-specific profiles of QT/RR hysteresis. Am J Physiol Heart Circ Physiol 295:H2356-H2363, 2008.

Akturk, A. and Goldsman, N. (2008) "Electron transport and full-band electron phonon interactions in graphene" J. of Applied Physics 103.

S. Paredes, T. Rocha, P. de Carvalho, and J. Henriques, "Atrial Activity Detection through a Sparse Decomposition Technique," vol. 2, pp. 358-362, 2008 International Conference on BioMedical Engineering and Informatics, 2008.

R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).

O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).

H. Li, R. Li, F. Wang. Multiresolution Subband Blind Source Separation: Models and Methods. Journal of Computers, vol. 4, No. 7 (2009), 681-688.

Afonso, V.X.; Tompkins, W.J.; Detecting ventricular fibrillation. IEEE Engineering in Medicine and Biology Magazine, vol. 14 , Issue: 2, pp. 152-159, (2014).

Dash S, Chon KH, Lu S, Raeder EA. Automatic real time detection of atrial fibrillation. Ann Biomed Eng. Sep. 2009;37(9):1701-9. Epub Jun. 17, 2009.

M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).

R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).

J. Piccini, et al, Predictors of sudden cardiac death change with time after myocardial infarction: results from the Valiant trial. European Heart Journal (2009).

J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).

S.Hadei, M. Iotfizad. A family of adaptive filter algorithms in noise cancellation for speech enhancement. International Journal of Computer and Electrical Engineering, vol. 2, No. 2, Apr. 2010. 1793-8163.

Allen, M., Tung, V., Kaner, R. (2010) "Honey Carbon: A Review of Graphene" Chem. Rev. 110:132-145.

Attila S. Farkas. et. al. Biomarkers and endogenous determinants of dofetilide-induced torsades de pointes in $\alpha$1-adrenoceptor-stimulated, anaesthetized rabbits. British Journal of Pharmacology. vol. 161, Issue 7, pp. 1477-1495, Dec. 2010.

HJ van der Linde, B Van Deuren, Y Somers, B Loenders, R Towart and DJ Gallacher, The Electro-Mechanical window: a risk marker for Torsade de Pointes in a canine model of drug induced arrhythmias, British Journal of Pharmacology (2010) 161 1444-1454.

Daubechies I., et al. Synchrosqueezed wavelet transforms: an empirical mode decomposition-like tool. Applied and Computational Harmonic Analysis, vol. 30, Issue 2, Mar. 2011, pp. 243-261.

M. Brockway and R Hamlin, "Evaluation of an algorithm for highly automated measurements of QT interval," Journal of Pharmacological and Toxicological Methods, vol. 64, pp. 16-24 (2011).

http://www.physionet.org/physiobank/database/#ecg, 2014.

http://www.physionet.org/physiobank/database/mitdb/, (2014).

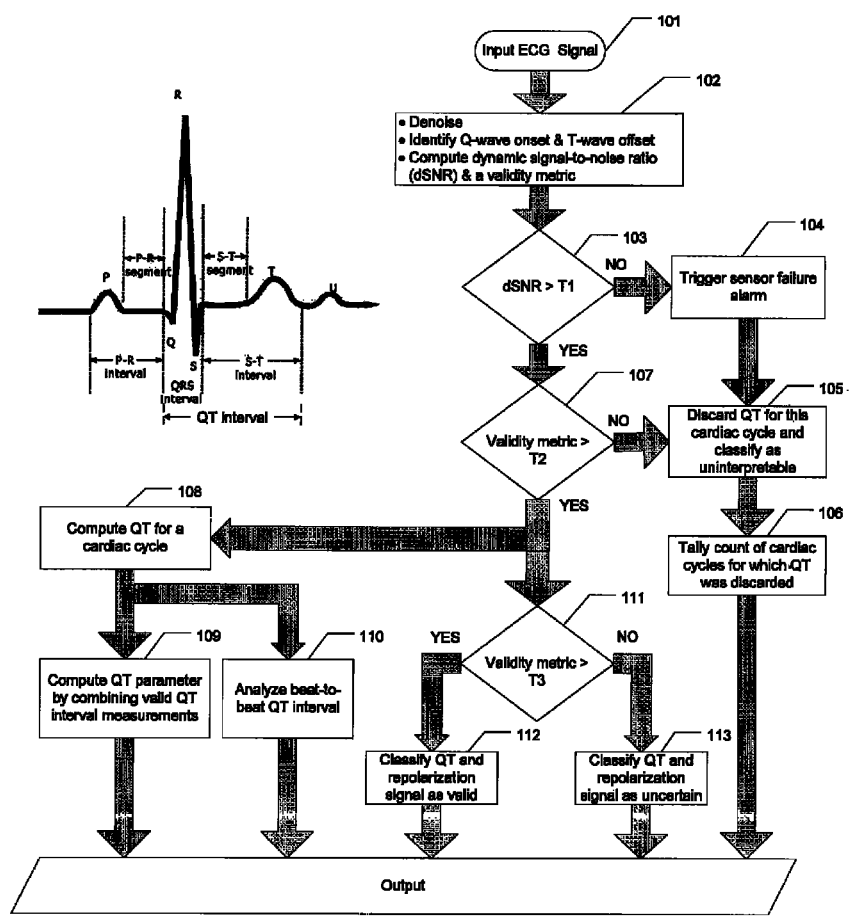

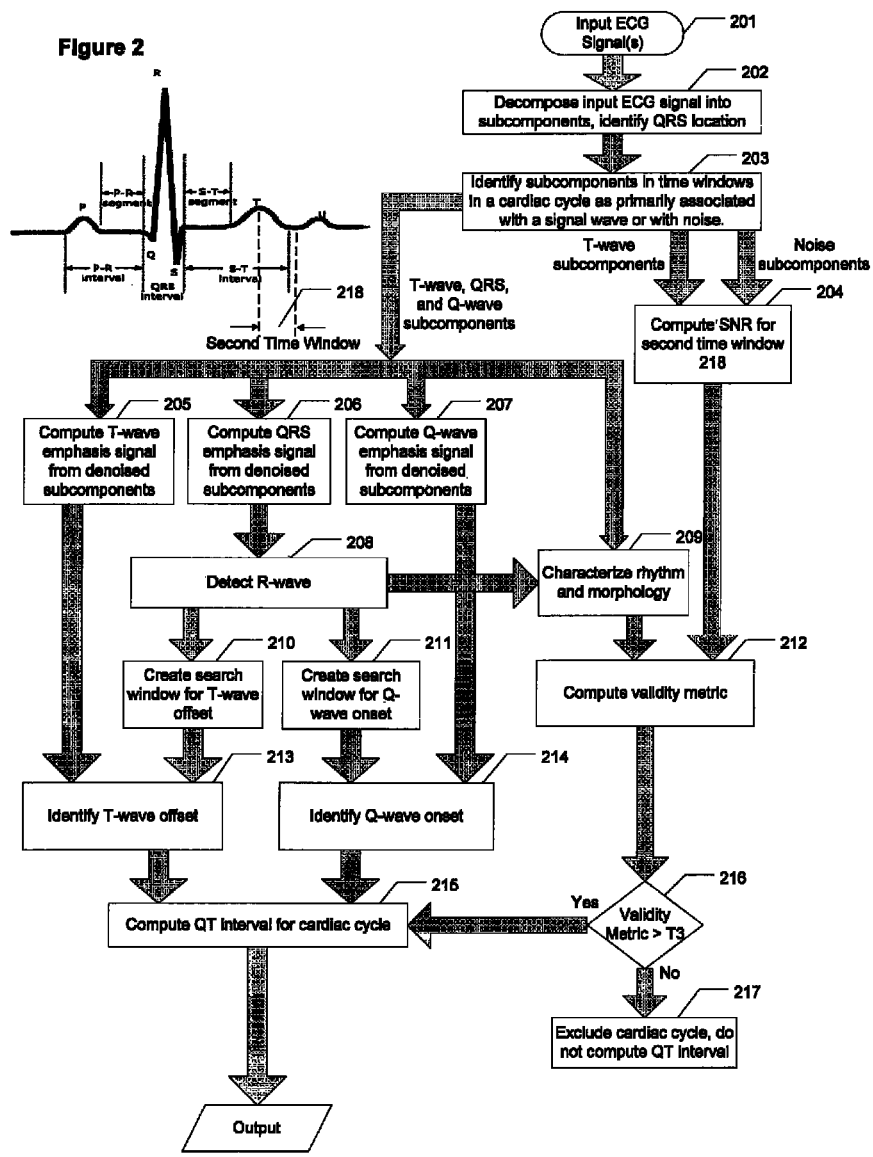

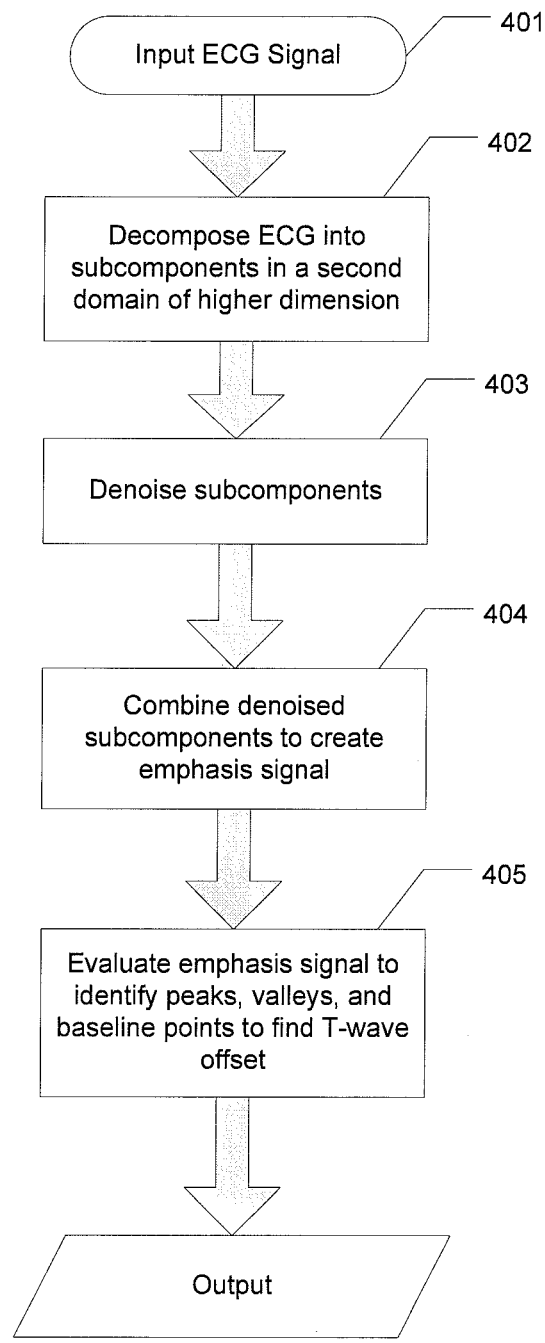
Figure 4 – Identify feature points with emphasis signals

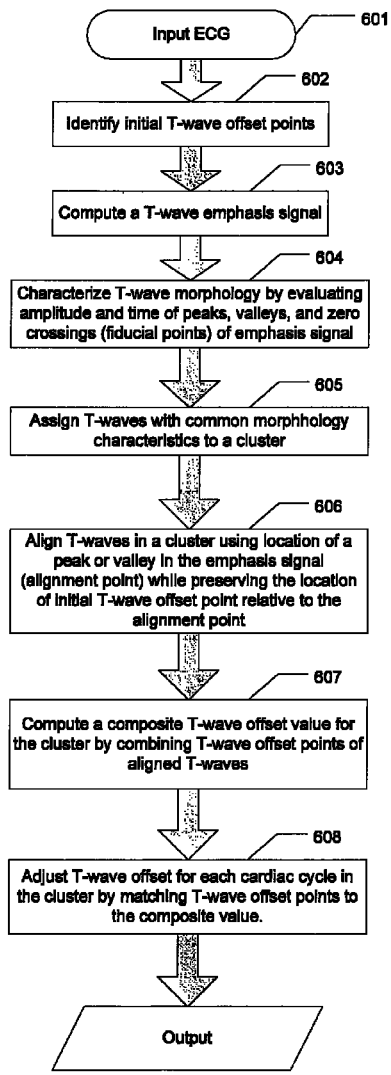
Figure 6 - Computing an adjusted T-wave offset

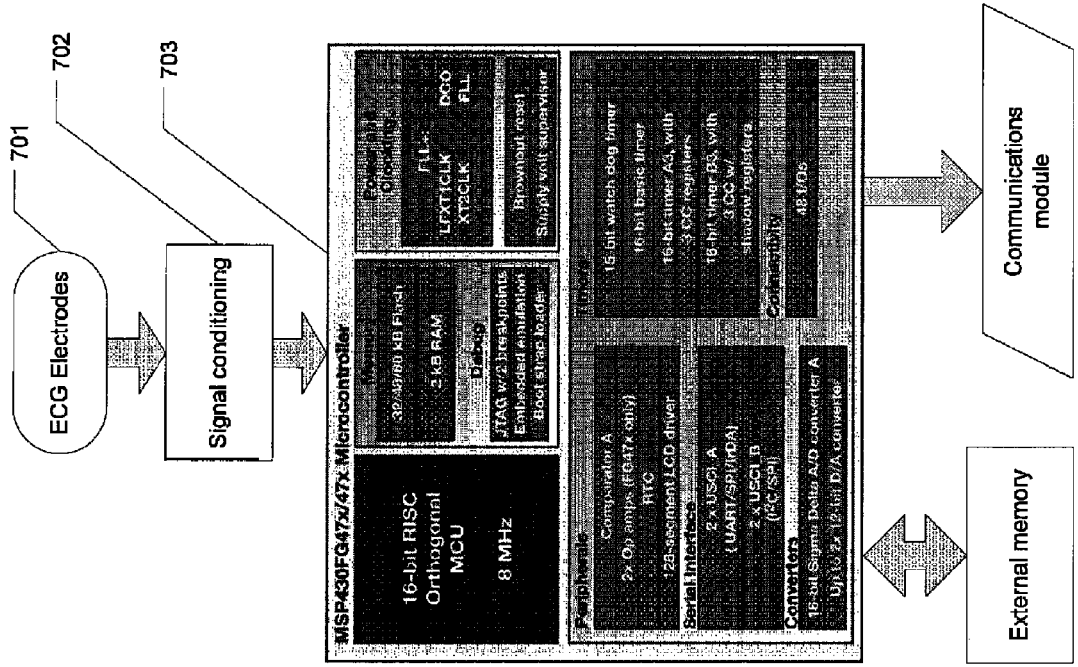
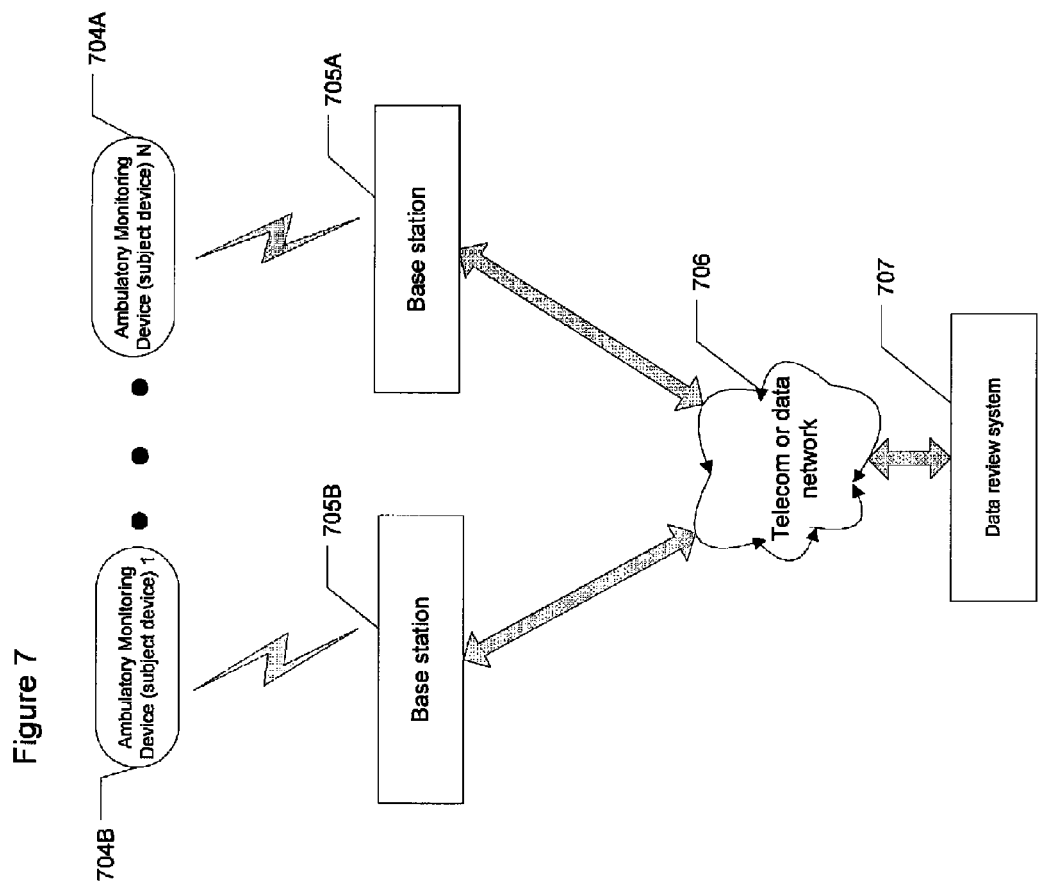
Figure 7

EXTRACTION OF CARDIAC SIGNAL DATA

RELATED PATENT DOCUMENTS

This patent document is a continuation under 35 U.S.C. §120 of U.S. patent application Ser. No. 13/172,415 filed on Jun. 29, 2011 (U.S. Pat. No. 8,433,395), which claims the benefit under 35 U.S.C. §119 of U.S. Provisional Patent Application Ser. No. 61/359,462, filed on Jun. 29, 2010, and 61/370,026, filed on Aug. 2, 2010; U.S. patent application Ser. No. 13/172,415 is also a continuation-in-part of U.S. patent application Ser. No. 12/938,995, filed on Nov. 3, 2010 (U.S. Pat. No. 8,632,465) and which claims the benefit of U.S. Provisional Patent Application Ser. No. 61/257,718, filed on Nov. 3, 2009, and of U.S. Provisional Patent Application Ser. No. 61/366,052, filed on Jul. 20, 2010, to all of which priority is claimed via 35 U.S.C. §120 for common subject matter; each of these patent documents is fully incorporated herein by reference.

FIELD OF INVENTION

The present invention relates to measurement of cardiac interval and extraction of other cardiac repolarization information from an ECG of human or animal subjects.

BACKGROUND

The cardiac repolarization period of the cardiac cycle, primarily consisting of the T-wave, is of interest for a variety of uses, including the analysis of cardiac function. For instance, repolarization abnormalities can be associated with dangerous arrhythmias, which are desirably detected for use in assessing cardiac function, ongoing health monitoring and/or treating cardiac pathologies. The QT interval (the time between the start of a Q-wave and the end of a T-wave) is frequently measured as an indicator of repolarization time with longer-than-normal or shorter-than-normal QT interval associated with possible risk of life-threatening arrhythmias. Evaluation of QT interval as an indicator of risk of life-threatening arrhythmias can involve measurement of average QT interval, QT interval dynamics, or both. Regulatory agencies can require that QT interval be measured in both animal models and human subjects during the course of developing new drugs as a means of assessing potential for drug-induced arrhythmias. QT interval measurements are also used to guide therapies in clinical care. Beyond measurement of QT interval, cardiac repolarization can be evaluated for clinical care and research using other methodologies including T-wave alternans, T-wave complexity, T-wave variability, and T-wave morphology changes.

Accurate measurement of QT interval has been challenging as a result of difficulties in accurately and consistently identifying T-wave offset due to its flat pattern, especially in the presence of noise. The accuracy of results produced by current methods is compromised, however, by noise in the ECG and by difficulty in accurately identifying T-wave offset. Further, approaches to identifying T-wave offset have suffered from an inability to accurately determine whether a particular T-wave offset is accurate, or whether the result may have been compromised due to the presence of noise, certain arrhythmias or difficult repolarization wave morphology. These and related matters have presented challenges to the measurement of QT interval, assessment of QT interval dynamics, and isolation of the cardiac repolarization signal of an ECG.

SUMMARY

Various aspects of the present invention are directed to devices, methods and systems involving evaluating repolarization activity of the heart as represented in the ECG of a human or animal subject, in a manner that addresses challenges including those discussed above.

In connection with various example embodiments, T-wave offset points for ECG signals are provided as an output, based upon a noise characteristic of an ECG signal in a second time window that includes at least a portion of the T-wave. In certain implementations, the location of a QRS complex in the ECG signal is identified and used for determining a first time window of the ECG signal in which to search for the T-wave offset point, and the T-wave offset point is identified within the first time window.

According to another example embodiment, a T-wave offset point is identified in an ECG. The ECG is decomposed into subcomponents in a second domain in which at least a portion of the subcomponents representing noise are independent of a portion of the subcomponents representing the signal. The noise and signal subcomponents are separated, which separation is used as a basis upon which the T-wave is provided.

The separation of the signal and noise subcomponents can be accomplished in a variety of manners. In some embodiments, the subcomponents are separated using one or more of spatially selective filtering, principal component analysis, independent component analysis and periodic component analysis. One or more subcomponents associated with the T-wave of the ECG are separated from other signal subcomponents within the second domain and used to evaluate a noise characteristic in the vicinity of the T-wave offset point.

According to another example embodiment, a noise characteristic is computed for a portion of the T-wave where the presence of noise can impact the accuracy of T-wave offset identification. The noise characteristic is computed by separating the T-wave energy and the noise energy in the portion of the T-wave and using the respective energies to compute a signal-to-noise ratio or other measures indicative of the relative levels of signal and noise energy in the portion. T-wave energy and noise energy in the portion can be separated by a number of techniques including band-pass filtering, wavelet thresholding, multidomain signal processing, or adaptive filtering.

According to another example embodiment, an emphasis signal is computed that exaggerates inflections in the signal and transition points of the emphasis and denoised signals, such as peaks, valleys, and baseline points, are detected to identify the T-wave offset point. These transition points may be detected in one or more of a variety of manners, using one or more approaches as described herein, such as via the analysis of subcomponents separated in accordance with the above.

According to another example embodiment, the subcomponents used to compute the emphasis signal are denoised using at least one of spatially selective filtering, principal component analysis, independent component analysis and periodic component analysis to improve consistency and accuracy of detecting transitions within the emphasis signal. In additional embodiments, the denoised subcomponents are used to reconstruct a denoised ECG.

According to another example embodiment, a validity-type metric is computed to assess the validity of a T-wave offset point, which can be used to automatically include the T-wave offset point as an output indicative of an accurate ECG characteristic. The validity metric is computed based on noise (e.g., using a dynamic signal-to-noise ratio) computed for a portion of the T-wave of a cardiac cycle as the ratio of energy in said signal subcomponents and noise subcomponents. In some embodiments, the validity metric is computed based upon the presence of ventricular or atrial fibrillation, ventricular tachycardia, an RR or QT interval outlier, QT dispersion and the degree of T-wave complexity.

According to yet another example embodiment, a cardiac repolarization signal is constructed by identifying T-wave offset and T-wave onset. A portion of an ECG between (or about between) T-wave onset and T-wave offset is isolated from the remainder of the ECG to construct a time series consisting primarily of repolarization activity, which can then be subsequently analyzed to evaluate T-wave alternans, T-wave morphology changes, T-wave complexity, T-wave variability, or other methods of analysis.

The above summary is not intended to describe each embodiment or every implementation of the present disclosure. The figures and detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which:

FIG. 1B provides an example high-level data flow for computing a QT interval, as may be implemented in connection with FIG. 1A, consistent with one or more example embodiments of the present invention;

FIG. 2 provides an example detailed data flow and decision diagram for computing a QT interval, consistent with one or more example embodiments of the present invention;

FIGS. 4, 4A, 4B and 4C provide an example data flow and decision diagram and related plots for identifying T-wave offset using an emphasis signal, consistent with one or more example embodiments of the present invention;

FIGS. 6, 6A, 6B and 6C provide example data flow block diagrams and example waveforms for a technique that provides a systematic adjustment of T-wave offset involving clustering of T-waves with similar morphology followed by alignment of T-waves within the cluster, consistent with one or more example embodiments of the present invention;

FIG. 7 provides an example embodiment of a system that employs a battery or passively powered subject device for collecting ECG in communication with a data collection or review system, consistent with one or more example embodiments of the present invention;

Figure 1A:
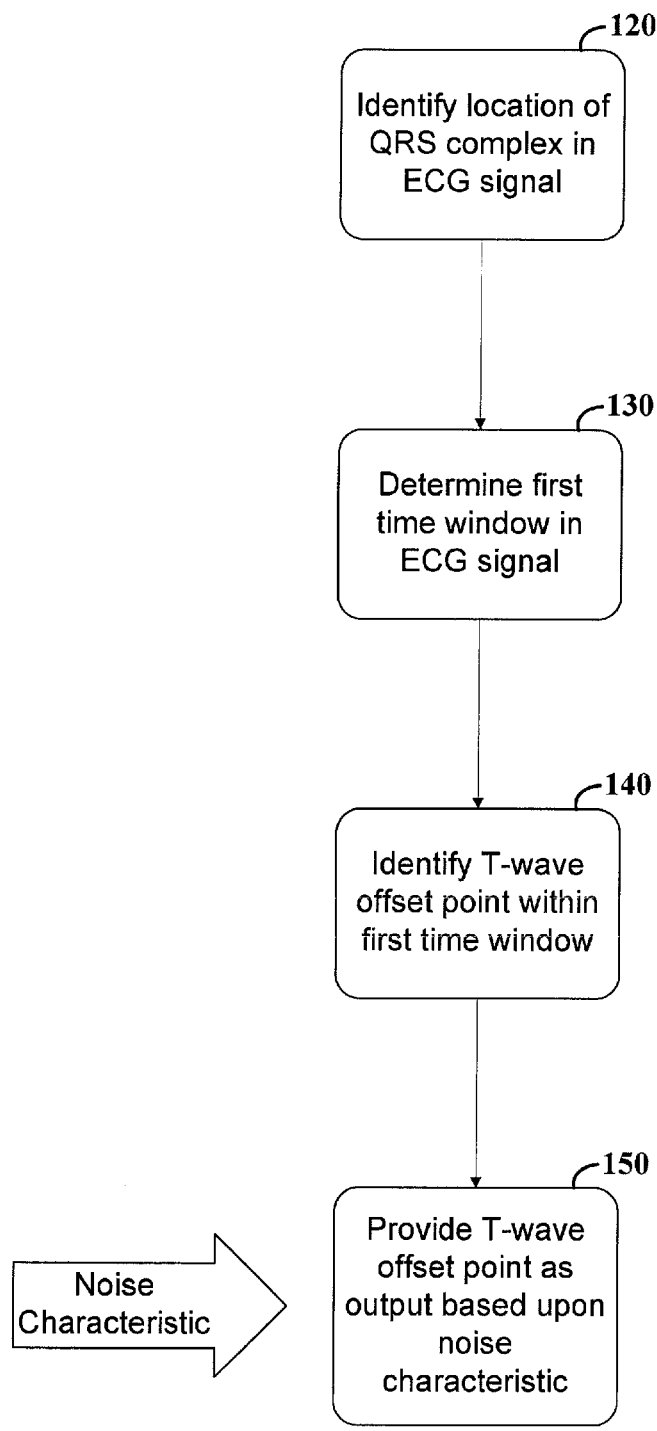
FIG. 1A is a data flow for an approach to providing a T-wave offset, consistent with one or more example embodiments of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention including aspects defined in the claims.

DETAILED DESCRIPTION

Aspects of the present invention relate to methods and devices for assessing repolarization activity. More particular aspects are directed to identifying accurate, consistent, and valid T-wave offset points within an ECG of human or animal subjects. Identification of accurate, consistent, and valid T-wave offset feature points in an ECG is useful in connection with measurement of QT interval and for creating a cardiac repolarization signal for evaluation of repolarization activity of a heart.

In connection with various embodiments of the present invention, accurate and consistent QT interval measurements are for a variety of applications such as those involving measurement of the QT interval of ambulatory subjects in environments susceptible to noise. The noise contained in these signals can vary in character and composition. For many applications, these signals include in-band noise whereby the spectral content of the noise overlaps with the spectral content of the ECG signal, which can present challenges to the detection/measurement and use of signals as discussed herein. In-band noise can be problematic because, unlike noise with spectral content outside the signal bandwidth, removing in-band noise without introducing distortion in the ECG signal can be particularly challenging. Various embodiments of the present invention are directed to the processing of signals having reduced in-band noise, to facilitate a determination of a validity-type aspect of the signals for evaluation thereof, and related provision of signals (e.g., as an output) with a relatively high degree of confidence in the validity of the signals. Certain embodiments are also directed to the reduction of in-band noise and, in many applications, reducing such in-band noise without significantly distorting the ECG signal. These embodiments may be implemented with the analysis of the portion of the ECG associated with cardiac repolarization, thereby improving the accuracy and consistency of subsequent analysis of repolarization activity.

The T-wave offset point can be selected and provided based upon one or more of a variety of approaches. In connection with one embodiment, a T-wave offset point of an ECG signal is provided as follows. The location of a QRS complex in the ECG signal is identified and used for determining a first time window of the ECG signal in which to search for the T-wave offset point. The T-wave offset point is identified within the first time window, and the identified T-wave offset point is provided as an output based upon a noise characteristic of the ECG signal in a second time window that includes at least a portion of the T-wave.

In other embodiments, the identified T-wave offset point is provided based upon a comparison of the noise characteristic to a threshold. Other embodiments are directed to providing the identified T-wave offset point based upon a presence, in the cardiac cycle, of at least one of: atrial fibrillation, QT dispersion in a multi-lead ECG exceeding a threshold, T-wave morphology complexity exceeding a predefined threshold, ventricular ectopy, a QT interval measurement that falls outside of a user-defined physiologic outlier value or a statistical outlier value. In certain embodiments, the identified T-wave offset point (or a plurality of such identified points) is used to assemble a time series of the provided QT interval values, which can be subjected to analysis of variability.

The second time window can be defined in one or more manners to suit various embodiments and applications, and may include the identified T-wave offset point. In some embodiments, the duration of the second time window can be set to about 30% of the duration of a nominal QT interval of the ECG signal, and extends beyond the T-wave offset point by about 10% of the nominal QT interval duration. In one example, the second time window may have a duration of about 50 msec and be centered on about (e.g., within a few milliseconds of) the identified T-wave offset point. In another embodiment, the second time window extends from about the point of a largest deflection of the T-wave from an isoelectric line of the ECG signal to (or near) the T-wave offset point. In other embodiments, the second time window includes a time period extending from about a QRS offset point in the ECG signal to about the T-wave offset point. In still other embodiments, the second time window includes a time period extending the full duration of a cardiac cycle in the ECG signal.

The noise characteristic may be obtained in one or more of a variety of manners, depending upon the application. In some embodiments, the noise characteristic is computed as follows. The ECG signal is decomposed into subcomponents, and subcomponents in the second time window are identified as primarily associated with either noise or the T-wave of the underlying ECG signal. A denoised signal is computed for the second time window by combining the subcomponents that are primarily associated with the T-wave. A noise signal is computed for the second time window by combining the residual subcomponents not primarily associated with the T-wave (e.g., the residual components being those not combined to form the denoised signal). The noise characteristic is then computed based upon aspects of the noise and/or denoised signal. For example, the noise characteristic can be computed using one or more of energy of the noise signal, standard deviation of the noise signal, zero crossing density of the noise signal, a metric of noise amplitude computed using an envelope of the noise signal, and a metric of energy of the denoised signal relative to energy of the noise signal. Further, metric of energy of the denoised signal relative to energy of the noise signal may be a signal-to-noise ratio of the ECG signal within the second time window.

In other embodiments, the noise characteristic is computed as follows. A denoised signal is computed for the second time window using at least one of a band-pass filter, wavelet thresholding, and an adaptive filter that passes primarily T-wave energy. A residual of the step of computing the denoised signal is captured as the noise signal for the second time window. The noise characteristic is computed based upon one or both of the noise and denoised signals, such as by using one or more of: energy of the noise signal, standard deviation of the noise signal, zero crossing density of the noise signal, a metric of noise amplitude computed using an envelope of the noise signal, and a metric of energy of the denoised signal relative to energy of the noise signal.

With respect to the above and other discussion herein, the term envelope, as applied to a noise signal by way of example, refers to a curve joining the successive peaks of the noise signal following smoothing or low-pass filtering. One approach for computing the envelope involves applying a Hilbert transform of the noise signal, computing the absolute value of the transform output, and then low-pass filtering the absolute values.

Another example embodiment is directed to a method for providing a repolarization signal for a cardiac cycle of an ECG signal. The location of a QRS complex in the cardiac cycle is identified and used to further identify T-wave onset and offset points in the signal, which are in turn used to respectively define the start and end of the repolarization signal for the cycle. A noise characteristic of the ECG signal is determined for a time window spanning from about the start to about the end of the repolarization signal, and the repolarization signal is provided as an output, based upon the determined noise characteristic. The noise characteristic can be determined using one or more of a variety of approaches, such as those discussed above.

In some implementations, the repolarization signal is provided as an output based upon a comparison of the noise characteristic to a threshold. In other implementations, the repolarization signal is provided as an output based upon the determined noise characteristic and the presence in the cardiac cycle of at least one of: atrial fibrillation in the ECG signal, a degree of QT dispersion exceeding a threshold when the ECG signal is a multi-lead signal, T-wave morphology complexity of the ECG signal exceeding a threshold, ventricular ectopy, and a QT interval measurement that falls outside of a user-defined physiologic outlier value or a statistical outlier value. In some implementations, the provided repolarization signal is appended to a matrix of repolarization signals in which a dimension of the matrix corresponds to the number of cardiac cycles of the ECG signal.

Another example embodiment is directed to a method for providing a time series of beat-to-beat QT interval values from a digitized ECG signal of an ambulatory subject. The location of a QRS complex and a Q-wave onset point of a cardiac cycle of the ECG signal are identified and used for determining a first time window of the cardiac cycle in which to search for a T-wave offset point for a T-wave in the cardiac cycle. The T-wave offset point is identified within the first time window, and a QT interval value is computed using the identified Q-wave onset point of the QRS complex and the identified T-wave offset point. The QT interval value is included in a time series of beat-to-beat QT interval values, based upon a noise characteristic of the ECG signal in a second time window that includes at least a portion of the T-wave. The noise characteristic can be computed in one or more of a variety of manners, such as described above. In various implementations, the series of beat-to-beat QT intervals consists of QT interval values having error due to noise that is less than 2.5% of the mean QT interval of the ECG signal, and generated using the aforesaid inclusion approach. Such an error condition can be achieved, for example, as facilitated by the use of a second time window, which may be limited to a range about the T-wave offset point, and further by the use of denoising approaches as discussed and/or referenced herein or in the above-noted patent documents to which benefit/priority is claimed.

In various implementations, energy that is not primarily associated with T-wave energy in the first time window of the digitized ECG signal is suppressed, prior to identifying the T-wave offset point. This suppression can be achieved using, for example, one or more of MDSP denoising, wavelet threshold denoising, band-pass filtering, and adaptive filtering.

The QT interval value is included in the time series of beat-to-beat QT interval values, based upon one or more conditions. In one implementation, the QT interval can be included based upon a comparison of the noise characteristic to a threshold value. In another implementation, the QT interval value is included based upon the noise characteristic and the presence, in the cardiac cycle, of at least one of: atrial fibrillation, ventricular ectopy, QT dispersion in a multi-lead ECG exceeding a threshold, T-wave morphology complexity exceeding a predefined threshold, ventricular ectopy, a QT interval measurement that falls outside of a user-defined physiologic outlier value or a statistical outlier value.

Various embodiments are also directed to implementing one or more approaches as discussed herein, via a computer circuit executing instructions to carry out the various functions. In some embodiments, instructions are executed to repeat the steps as discussed herein to compute a plurality of QT interval values. Each QT interval value is included in a time series of beat-to-beat QT interval values based upon a comparison of a noise characteristic of a corresponding ECG signal in the second window to a predefined threshold.

For general information regarding exemplary aspects including performance aspects, as may be effected and/or realized in connection with various embodiments of this invention for providing beat-to-beat QT intervals, reference may be made to M. Brockway and R Hamlin, "Evaluation of an algorithm for highly automated measurements of QT interval," Journal of Pharmacological and Toxicological Methods, 2011, Article in press., doi:10.1016/j.vascn.2011.05.004, which is fully incorporated herein by reference.

Many embodiments described here are directed to signal processing approaches that may be implemented in accordance with those referred to as Multi-Domain Signal Processing (MDSP), and Multi-Domain Filtering (MDF) that uses MDSP to denoise physiologic signals, as exemplified in U.S. patent application Ser. No. 12/938,995, entitled "Physiological Signal Denoising," which is referenced above and fully incorporated herein by reference. Various embodiments may implement noise filtering and signal denoising using one or more approaches as described therein.

In the following discussion, reference is made (in brackets) to numbered references listed in order near the end of this document, which are fully incorporated herein by reference. These references may assist in providing general information regarding a variety of fields that may relate to one or more embodiments of the present invention, and further may provide specific information regarding the application of one or more such embodiments. Accordingly, one or more embodiments as described herein may be implemented in accordance with, or otherwise using, information, approaches, devices and systems as may be described in these references.

Turning now to the figures, and referring to FIG. 1A, a data flow diagram exemplifies approaches for providing a T-wave offset, consistent with one or more example embodiments of the present invention. At block 120 the location of a QRS complex in the ECG signal is identified, and the identified location is used at block 130 for determining a first time window of the ECG signal in which to search for the T-wave offset point. At block 140, the T-wave offset point is identified within the first time window, and the identified T-wave offset point is provided as an output at block 150, based upon a noise characteristic of the ECG signal in a second time window that includes at least a portion of the T-wave. Various embodiments and implementations as discussed above (and otherwise herein) may be implemented in connection with the approach shown in FIG. 1, including those directed to obtaining and using a noise characteristic.

According to example embodiments involving the computation of a QT interval, and referring to FIG. 1B, an input ECG signal 101 is denoised and Q-wave onset and T-wave offset points are identified using the denoised ECG in process 102. In many embodiments, ECG signal 101 has been filtered to remove noise energy outside the bandwidth of the sensed electrical activity of the heart and has been digitized using an analog-to-digital converter. Such filtering can be accomplished using a variety of well known methods and the passband of the filter will vary depending upon the species. As an example, a passband often used for human ECGs is 0.05 to 100 Hz. In some embodiments, a dynamic signal-to-noise ratio (dSNR) and a validity metric (VM) are computed in process 102 and used to assess the validity of the onset and offset points as well as ECG sensor integrity. In some embodiments, dSNR and VM are computed for a portion of the T-wave where the presence of noise can impact the accuracy of T-wave offset detection. In other embodiments, VM can be computed for a complete cardiac cycle. VM is evaluated relative to predetermined thresholds, T1, T2 and T3, in decision processes 103, 107 and 111 where T3>T2>T1. Evaluation of the VM is useful to determine the disposition of the information derived from a cardiac cycle and in particular, can be useful in determining if the information should be retained, discarded, or if there is value in having a human being review the QT interval measurement result provided by the algorithm. In some embodiments, the QT interval is computed if the VM>T2, and is otherwise classified as uninterpretable in process 105 (e.g., the T-wave offset information for that cardiac cycle cannot be determined). Cardiac cycles determined as being uninterpretable may generally refer to signals that have a noise and artifact level that is so high that review by a human being will render no additional useful information. In some embodiments a count of cardiac cycles is tallied, in process 106, that are determined to be uninterpretable (e.g., VM<T2 and/or discarded) as an indicator of signal quality.

If VM for a particular cardiac cycle is greater than T2 but, in decision process 111, is found to be less than T3, then the information for that cardiac cycle is classified as uncertain in process 113 and may be flagged for later review by a human being. If, in decision process 111, VM>T3 then the information for that cardiac cycle is classified as valid in process 112. In some embodiments, QT interval measured for those cardiac cycles classified as valid is considered to be sufficiently accurate and consistent that review by a human being adds no additional value or accuracy improvement, and those QT interval measurements are hence derived in a fully automated manner and without any human intervention.

In some embodiments, cardiac cycles classified as uncertain are recommended for review by a human being. The ECG for cardiac cycles classified as uncertain may be visually displayed to a human being along with the marker location for Q-wave onset and T-wave offset. The human operator can then accept the markers as determined by the algorithm, discard the cardiac cycle computing a QT interval, or move a marker if it is believed to be incorrectly placed by the algorithm.

In some embodiments, a time series of beat-to-beat QT interval values is further analyzed using techniques such as QT interval alternans and QT interval variability as markers of arrhythmogenic risk. In various embodiments, techniques used to analyze beat-to-beat QT interval measurements include root mean square of successive differences, standard deviation of successive differences, short-term variability using a mean of successive differences, long-term variability computed as the length of the long axis of the ellipsoid of a Poincaire plot, and multiscale entropy. In another embodiment, valid QT values are averaged over a predetermined time period (e.g., 30 seconds) to compute a mean QT interval.

In some embodiments a sensor failure alarm is triggered if the ECG is excessively noisy or if the ECG signal is absent. Either of these conditions can lead to a very low dSNR. This may indicate that an electrode has become loose or has fallen off the subject, or it may indicate that a lead connecting the electrode to a monitoring device may have been broken. In these embodiments dSNR is compared to a threshold T1 in decision process 103 and if dSNR is <T1, a sensor failure alarm is triggered in process 104. In some embodiments, the sensor failure alarm is only triggered after dSNR has remained below threshold T1 for a predetermined period of time in order to reduce the risk of false alarms.

According to other example embodiments, FIG. 2 shows more detailed approaches for computing the QT interval. In an example embodiment, an input ECG signal 201 is present in a first domain and is composed of an underlying ECG signal and a noise signal. For the purposes of this explanation, underlying ECG signal refers to the sensed electrical activity generated by the heart. Noise signal refers to sensed electrical activity generated by noise sources independent of the heart such as muscle EMG and measurement artifact caused by dynamic changes in electrical properties of the tissue-electrode interface of the sensor. Signal 201 is decomposed into subcomponents in a second domain of higher dimension than the first domain in process 202. In some embodiments, decomposition is accomplished using a discrete cosine transform [1], Fourier transform [2], filter bank [3], Gabor transform [4] or Karhunen-Loeve transform [5, 6]. In another embodiment, decomposition is accomplished using a wavelet-related transform and the decomposition levels correspond to wavelet scales [7]. In another embodiment, decomposition is achieved by representing the observed signals as a linear combination of basis functions. Signal decomposition embodiments and the use of subcomponents derived from the decomposition for denoising (i.e. removal of at least some of the in-band noise contained in the signal), extraction of information from the signal, and evaluation of the accuracy of extracted information is referred to as Multi-Domain Signal Processing (MDSP) by way of example, in the discussion herein. Use of MDSP techniques for removal of in-band noise from a signal is referred to as Multi-Domain Filtering (MDF), also by way of example.

Subcomponents are evaluated in process 203 to determine if those contained within a defined time window are primarily associated with noise or primarily associated with the underlying ECG signal. Each ECG signal wave (e.g., R-wave, Q-wave, T-wave, and P-wave) contributes energy to one or more subcomponents. The association of a set of one or more subcomponents with a particular signal wave (e.g., T-wave, QRS-wave, and P-wave) pertains to the representation of energy contained within a signal wave within the associated subcomponents [8]. In some embodiments, spatially selective filtering is employed. In this embodiment the subcomponents associated with the underlying ECG change during the time course of the cardiac cycle. Spatially-dependent selection of subcomponents within the cardiac cycle is determined according to time location of the subcomponents relative to the QRS complex. For example, once a QRS complex is identified, the approximate location of the T-wave is known. Subcomponents primarily associated with T-wave energy are selected as related to the underlying ECG signal during the time spanning the approximate T-wave location, and those subcomponents not associated with T-wave energy during this time span are said to be primarily associated with noise. Subcomponents may contain both energy of the underlying ECG signal and noise energy. For the purpose of this discussion, subcomponents are said to be associated with a particular signal wave of the ECG if more than about 50% of the energy in the subcomponent is energy of the underlying ECG signal wave.

Determining whether a subcomponent is primarily associated with noise or ECG signal, or denoising the subcomponents within the second domain, can be accomplished by using one or more of principal component analysis (PCA), independent component analysis (ICA), periodic component analysis (πCA) and spatially selective filtering (SSF). PCA and ICA are applicable to multi-lead ECG, while πCA and SSF can be applied to either multi-lead or single-lead ECG. The PCA technique [9, 10] uses subcomponent covariance information to orthogonalize subcomponents. The orthogonalized subcomponents with low signal power are often associated with noise and can be removed to achieve denoising. PCA can be used as a preliminary step prior to applying an ICA technique. The ICA technique further separates signal and noise sources [11] as a solution of an optimization problem that maximizes independence between them. The πCA technique computes and jointly diagonalizes covariance and autocorrelation matrices of subcomponents to separate them based on their periodicity or quasi-periodicity. [12, 13] The πCA technique extracts most periodic subcomponents corresponding to ECG rhythm and, since noise is not generally periodic, it is left behind.

SSF techniques [14, 15, and 16] detect signal-related features and pass them across the subcomponents while blocking features inherent to noise, relying upon the differences of noise and signal distributions across decomposition levels. In one embodiment, an SSF approach is used to exploit the fact that most noise subcomponents are confined to decomposition levels that represent high frequencies. In this embodiment, the locations of signal features are identified by examining subcomponents corresponding to lower frequency. The QRS location is identified, and a QRS window surrounding the detected QRS wave is created. The subcomponents associated with high frequencies are preserved within the QRS time window. The remainder of the cardiac cycle is assigned to a second time window where the high-frequency subcomponents are zeroed. QRS wave location for creating the first time window can be identified as high amplitude changes in peaks and valleys that occur simultaneously across multiple decomposition levels associated with lower frequencies. Techniques such as correlation or multiplication of these low-frequency subcomponents can be useful for computing an emphasis signal that provides for improved detection of the QRS complex in a noisy ECG. The subsequent emphasis signal can be passed through a constant or adaptive threshold detector to locate the QRS complex.

In another embodiment, some artifacts can be detected as large peaks present in subcomponents corresponding to high frequency. These artifacts can then be removed by zeroing subcomponents where the large peaks were detected. By zeroing out the subcomponents or time segments within subcomponents associated with noise, and reconstructing the ECG signal using those subcomponents associated with the ECG signal, the in-band noise level in the ECG is substantially reduced, or "denoised", to create a denoised ECG. A denoised signal can be reconstructed by performing the inverse of the transform used to decompose the signal on the denoised subcomponents. For general information regarding example denoising techniques that can be used in this and related embodiments, reference may be made to U.S. patent application Ser. No. 12/938,995, referenced above.

In some embodiments signal energy relative to the noise energy in second window 218 is computed as a signal-to-noise ratio (SNR) as in process 204. In one embodiment second window 218 spans from about the T-wave peak to shortly after the T-wave offset point. In other embodiments, the duration of second window 218 is a percentage of the QT interval, 30% for example. In this embodiment ⅔ of the duration of window 218 spans before T-wave offset and ⅓ extends after T-wave offset. In another embodiment, window 218 has a fixed duration for a given species. For example, for human beings window 218 may be about 50 msec in duration and is approximately centered on the T-wave offset point.

Figure 8:
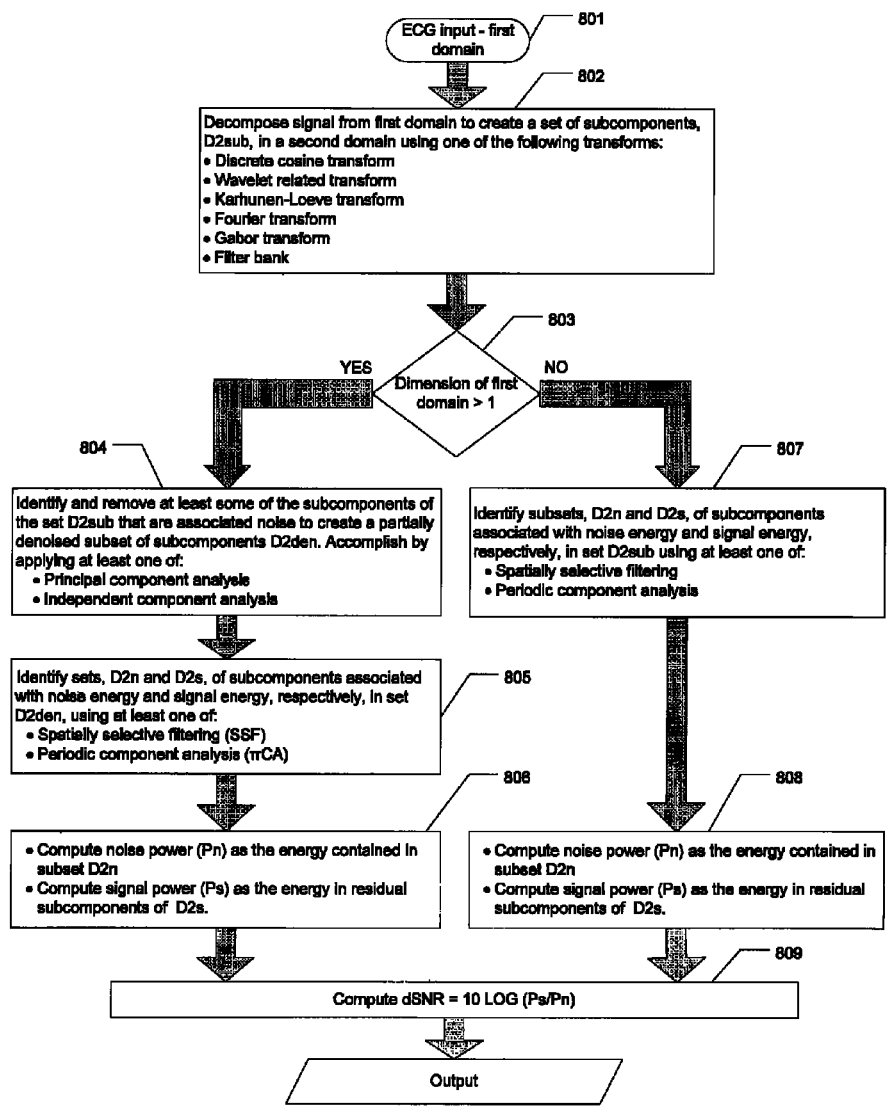
FIG. 8 provides an example data flow diagram for computing a dynamic signal-to-noise ratio, according to another example embodiment of the present invention.

In one embodiment, referring to FIG. 8, SNR (dSNR) is computed as the ratio of the energies in signal and noise subcomponents. Input signal 801 in a first domain is decomposed into subcomponents, referred to as set D2sub, in a second domain of higher dimension in process 802.

The dimension of the first domain is evaluated in decision process 803. If the dimension of the first domain is larger than 1 then a PCA or ICA technique can be used to identify at least some of the subcomponents primarily associated with noise in process 804. The noise subcomponents extracted at this initial denoising step are discarded and the residual noise and signal subcomponents are evaluated using SSF or πCA in process 805. The noise subcomponents identified in process 805, D2n, are used to compute an estimate of noise energy in process 806. The residual subcomponents, D2s, are used to compute an estimate of signal energy in process 806.

If the dimension of the first domain evaluated in decision process 803 equals 1 (e.g., a single channel ECG signal), then subcomponents primarily associated with noise, referred to as set D2n, are identified using SSF or πCA in process 807. The residual subcomponents, D2s, are those primarily associated with an underlying ECG signal. In these contexts, signals primarily associated with noise are those signals having an energy value of which at least half is from noise components. Similarly, signals primarily associated with an underlying ECG signal are those having an energy value of which at least half is from an underlying ECG signal. In process 808, an estimate of noise energy is computed using subcomponents D2n and an estimate of signal energy is computed using subcomponents D2s.

Once noise energy and (underlying ECG) signal energy are computed in processes 806 and 808, dSNR is then computed in process 809 according to formula:

$$SNR_{dB} = 10\log_{10}\left(\frac{P_{signal}}{P_{noise}}\right);$$

where $P_{signal}$ and $P_{noise}$ are respective signal and noise energy. Using this approach, dSNR can be updated on a sample-by-sample basis, and can likewise be computed for a group of sample points or a time window. In one embodiment dSNR is computed for each cardiac cycle. In other embodiments, dSNR is computed for a time window surrounding the location of a detected feature point (e.g., T-wave offset) and can be used to assess validity of the detected feature point. Alternate embodiments may involve updating dSNR more or less often. For example, it may be useful in some embodiments to compute a value of dSNR for a window of two to ten cardiac cycles and use this value in calculation of the validity metric for all cardiac cycles within the window.

In other embodiments, signal-to-noise ratio is estimated using conventional approaches following denoising of the signal using an MDF-based embodiment as discussed herein, or using conventional approaches in combination with the approach(es) described in FIG. 8. In one embodiment, the noise is measured between signal waves by computing the peak amplitude and density of zero crossings. In other embodiments, a signal-to-noise ratio is estimated by computing a spectral distribution of the denoised ECG signal. In this embodiment, peaks in the spectral distribution are evaluated to determine the relative power in the spectrum that occurs within and outside of the normal range of the QRS complex, T-wave, and P-wave.

In various example embodiments, and referring to FIG. 2, subcomponents are used to compute T-wave (process 205), QRS (process 206), and Q-wave (process 207) emphasis signals that exaggerate peaks, valleys and slopes of an ECG wave for identifying feature points. As an example, R-wave identification is accomplished by generating a QRS emphasis signal that highlights the significant slopes of the R-wave by combining subcomponents associated with the R-wave. Likewise, T-wave offset identification is achieved by computing an emphasis signal from subcomponents associated with the T-wave.

The specific subcomponents associated with the R-wave, Q-wave, or T-wave depend upon the decomposition technique used, sampling rate, frequency content of the signal wave, and the species from which the ECG was recorded. As an example, when decomposition is accomplished using a discrete wavelet-related transform of a human ECG sampled at 250 Hz, the associated R-wave subcomponents correspond to wavelet scales $2^1$ through $2^4$. The associated T-wave subcomponents for this same scenario correspond to wavelet scales $2^3$ to $2^5$. In this example, the set of subcomponents associated with R-waves and T-waves overlap and are discriminated based on temporal occurrence by creating a search window relative to the QRS complex in process 210. In one embodiment, all subcomponents associated with a signal wave are combined to create the emphasis signal. In another embodiment, a subset of these subcomponents is used to compute the emphasis signal. In one embodiment, evaluation of the emphasis signal to detect a feature point is accomplished using techniques described by Martinez et al [8] based upon examination of the pattern of significant peaks, valleys, and zero crossings within the emphasis signal. In one embodiment or process 208, the R-wave is detected by applying an adaptive threshold technique [17] to the emphasis signal. In one embodiment of process 213, T-wave offset is identified as the first baseline point after the last significant peak or valley of the T-wave emphasis signal. In another embodiment a combination of the emphasis and denoised signals are used to detect feature points.

To identify Q-wave onset in process 214, a search window is created in process 211 to identify a time window relative to the R-wave where Q-wave onset is expected to occur. The denoised subcomponents associated with the QRS-wave are used to compute an emphasis signal in process 207 that is subsequently evaluated to identify the Q-wave onset point in process 214. In one embodiment, Q-wave onset is identified as the last baseline point prior to the first significant peak or valley of the QRS-wave emphasis signal. To improve the accuracy of identifying T-wave offset and Q-wave onset, search windows are created relative to the location of the R-wave in processes 210 and 211 to limit identification of the offset and onset times to windows in time within the cardiac cycle where it would be reasonable for the respective onset and offset to occur.

Once Q-onset and T-offset are identified in processes 213 and 214, QT interval is computed in process 215. In some embodiments, a determination is made as to whether the QT interval is accurate and valid. This can be accomplished by computing a validity metric (VM) in process 212 and then comparing the validity metric to a threshold T3 in decision process 216. If VM>T3, then the QT interval computed in process 215 is considered valid. If not, then the QT measurement for that cardiac cycle is discarded as in process 217. The validity metric computed in process 212 is a function of dSNR computed in process 204 and rhythm and morphology characteristics computed in process 209. Rhythm and morphology characteristics may include characteristics indicative of the presence of atrial fibrillation, QT dispersion when the ECG signal is a multilead signal, and complexity of T-wave morphology. In some applications, such as when computing a cardiac repolarization signal, the validity metric is modulated based upon the presence of ventricular ectopy such that a repolarization wave is excluded for a cardiac cycle containing a ventricular ectopy. In some applications where QT interval is computed, including QT measurements from cardiac cycles containing ventricular ectopy may improve the predictive value of QT variability assessments [18]. In this application it would therefore not be desirable to modulate VM as a function of the presence of ventricular ectopy.

In an alternate embodiment, the ECG is denoised using MDF techniques and the feature points of Q-wave onset and T-wave offset can be evaluated using traditional techniques in order to measure QT interval. This approach can be useful in some applications because the accuracy of feature point identification can be improved by using a denoised ECG. In another embodiment, it is possible to compute T-wave offset using an MDSP embodiment described above and compute Q-wave onset from a denoised ECG using traditional techniques. As an example, Q-wave onset can be identified using either threshold, derivative-based, or pattern matching methods applied to the denoised ECG signal. In the threshold method, a region that precedes the first peak or valley associated with R-wave where at least a few samples are below a pre-specified threshold is found. The Q-wave onset is determined as a last point in the identified region. In the derivative-based method an emphasis signal is computed by differentiating the denoised ECG. A region in the emphasis signal is identified preceding the first peak or valley associated with the R-wave emphasis signal where at least a few samples are below a predetermined threshold. The Q-wave onset is identified as the last point in the region.

A pattern or template matching method can also be applied to the denoised ECG. In this approach, a user selected or signal averaged template of the ECG of a representative cardiac cycle is created and subsequently cross-correlated with the ECG to be analyzed. In another embodiment a template can be automatically generated by signal-averaging cardiac cycles for which VM>T3. The QRS onset is identified in the template either manually by the user, by using threshold techniques or by derivative based method applied to the template. Once Q-wave onset is identified in the template, the template is cross-correlated with cardiac cycles of the ECG to be analyzed. The template is shifted in time to maximize the cross-correlation function of the full cardiac cycle. In some embodiments, the template can be further shifted to improve the cross correlation between Q-waves of the cardiac cycle under evaluation and the template. The QRS onset is identified from the matched template.

Figure 3:
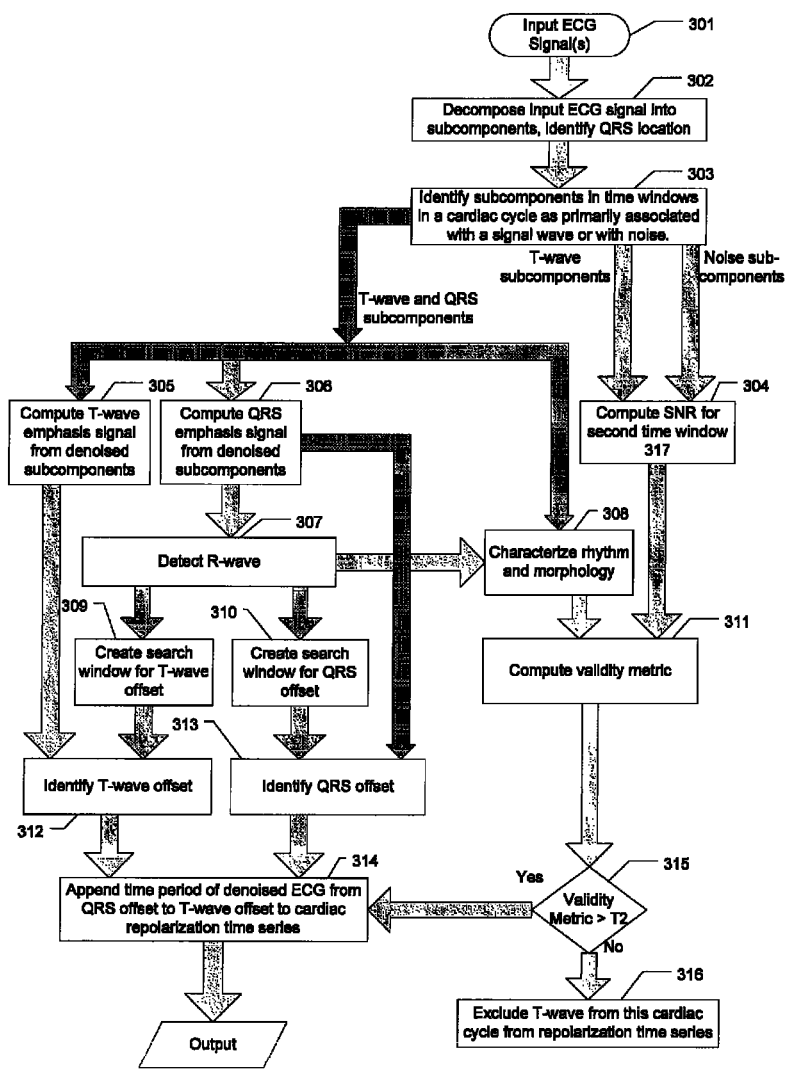
FIGS. 3 and 3A provide an example data flow and decision diagram and related plots for creating a cardiac repolarization signal, consistent with one or more example embodiments of the present invention.
Figure 3A:
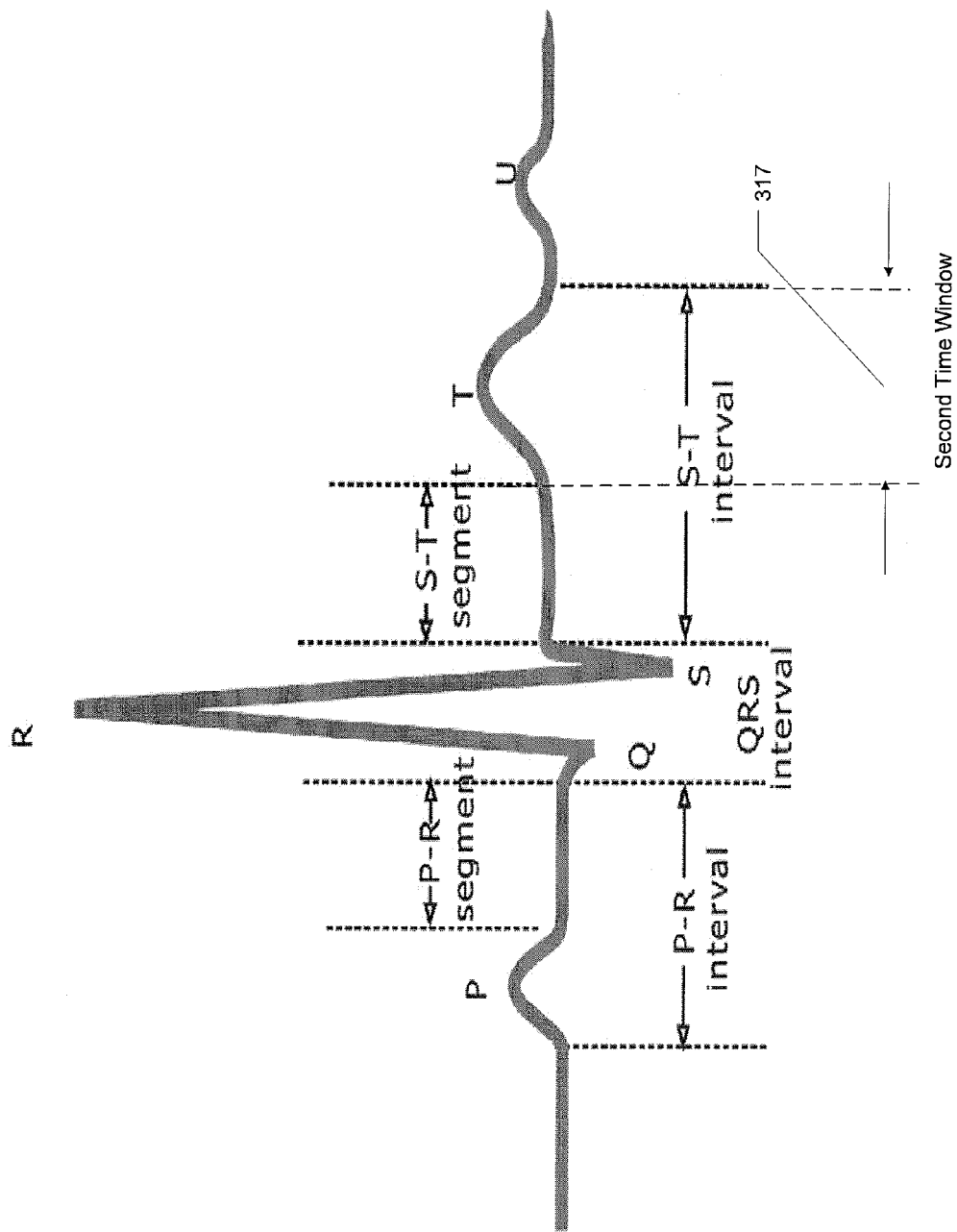

Various embodiments are directed to creating a cardiac repolarization signal. In an example embodiment, and referring to FIGS. 3-3A, a cardiac repolarization signal is constructed by isolating the portion of the ECG signal corresponding to the T-wave and suppressing (actively or passively) all other signal waves (e.g., QRS complex, P-wave) and noise. In some embodiments, all or most of the activity in a plurality of cardiac cycles is suppressed except for the T-wave, or repolarization wave, and T-waves from multiple cardiac cycles are aligned sequentially to form a time series representing a cardiac repolarization signal. In another embodiment, the isolated T-waves are joined together to form a time series representing a cardiac repolarization signal. In another embodiment a cardiac repolarization signal consists of organizing the isolated T-waves into a matrix. The length of rows in the matrix is determined by the sampling rate and the length of the longest T-wave and the number of rows is determined by the number of valid T-waves in the ECG segment for which repolarization activity is to be analyzed. The matrix rows containing T-waves can be padded with zeros or the isoelectric ECG value to match the longest T-wave in the segment. The T-waves in the matrix can be aligned by their peak. In some implementations, a signal that consists primarily of ventricular repolarization activity is created using these approaches to facilitate analysis of the repolarization activity of the heart independent of atrial activity and ventricular depolarization activity and mitigate potential issues with the high level of spectral energy in the QRS complex leaking into the bandwidth of the T-wave and biasing the result.

In connection with other embodiments, a denoised cardiac repolarization signal is created to facilitate the use of several analysis methods that can identify and evaluate repolarization abnormalities and can potentially improve the accuracy of results provided by these methods of analysis. These analysis methods include T-wave alternans, T-wave variability, T-wave morphology changes, and T-wave complexity. In various embodiments, beat-to-beat variability of T wave parameters is measured using one or more of the following metrics [18, 19, and 20]:

Standard Deviation of T wave parameter from N consecutive beats=SD

Root mean square of N successive differences of the T wave parameter=RMSSD

Standard deviation of N successive differences of the T wave parameter SDSD

Beat-to-beat variability of successive differences measured as $2*SD^2-1/2*SDSD^2$ Short-term variability of the T wave parameter, $$STV_D = \sum_{i=1}^{N} |D_{n+1} - D_n| / [N\sqrt{2}],$$

where $D_n$—is a T wave parameter from $n^{th}$ beat

Long-term variability of the T wave parameter:

$$LTV_D = \sum_{i=1}^{N} |D_{n+1} + D_n - 2D_{mean}| / [N\sqrt{2}],$$

where $D_n$—is a T wave parameter from $n^{th}$ beat

In another embodiment nonlinear measures of complexity of repolarization dynamics such as multiscale entropy [21] are computed to measure variability beyond a single beat lag.

In one embodiment a denoised cardiac repolarization signal is created by isolating the T-wave in a series of cardiac cycles that have been denoised using MDF. T-wave isolation is accomplished by identifying the onset of the T-wave (T-wave onset), the offset of the T-wave (T-wave offset), and then removing those portions of the ECG that fall outside the time between T-wave onset and offset of a cardiac cycle (or otherwise using the portions of an ECG signal lying within a time window generally extending from the T-wave onset to offset). One or more of the steps employed for isolating the repolarization wave for a cardiac cycle can be accomplished in a manner consistent with the embodiments described for measuring QT interval for a cardiac cycle. In one embodiment, and referring to FIG. 3, input signal 301 is decomposed into subcomponents and the QRS location is identified in process 302. Subcomponents are evaluated to identify those primarily associated with noise and those primarily associated with signal waves of the underlying ECG signal in process 303 using methods described earlier relating to process 203. Processes 302 and 303 are the same as processes 202 and 203, respectively, from FIG. 2. T-wave and QRS emphasis signals are computed in processes 305 and 306 in a manner such as that described for processes 205 and 206. Likewise, the QRS emphasis signal is evaluated to detect R-waves in process 307 in a manner such as described in process 208. Similarly, a T-wave offset search window is created in process 309 and a QRS offset search window can be created in process 310 in a manner such as in processes 210 and 211, respectively. T-wave offset is identified in process 312 in the same manner as in process 213. In one embodiment, the beginning of the repolarization wave is identified as QRS offset. QRS offset is identified in process 313 by evaluating the QRS emphasis signal to find the first baseline point after the last significant slope associated with the QRS complex. In an alternate embodiment, the beginning of the repolarization wave is the T-wave onset point and is identified as the last baseline point prior to a first significant peak or valley of the T-wave emphasis signal computed in process 305. In another embodiment, T-wave emphasis and denoised signals can be used to identify T-wave onset.

In some embodiments, a validity metric (VM) is computed to determine if a repolarization wave from a cardiac cycle should be included in the repolarization signal. Computation of the validity signal for deciding if a repolarization wave should be included or not is accomplished in a manner consistent with that for computing VM for a QT measurement. A signal-to-noise ratio (SNR) is computed in process 304 for second time window 317. In one embodiment, second time window 317 spans from about the T-wave onset point to about the T-wave offset point. Other embodiments are directed to a time window including a larger or lesser portion of signal including the T-wave. Rhythm and morphology are characterized in process 308 and this information is combined with SNR to compute VM in process 311. In some embodiments the value of VM is modulated according to whether a cardiac cycle contains a ventricular ectopic beat.

The accuracy of results obtained from various analysis methods applied to a repolarization signal can be impacted by the presence of noise and one or more artifacts. In some embodiments, any T-wave obtained from a cardiac cycle is excluded from the cardiac repolarization signal, when the level of noise or artifact(s) is high enough to impact the accuracy of information derived from the repolarization wave. In one embodiment, a validity metric is computed and only T-waves from those cardiac cycles where the validity metric is >T3 are included in the construction of the repolarization signal. In an alternate embodiment, the repolarization signal from a cardiac cycle may be classified as valid, uncertain, or uninterpretable according to the value of VM, in a manner similar to that used to classify and handle QT measurement for a cardiac cycle. Cardiac cycles classified as uncertain may be reviewed by a human being to determine if the T-wave for that cardiac cycle should be excluded from the repolarization signal, or whether it should be included with T-wave onset and offset as marked, or whether the onset or offset time for the T-wave should be modified. When creating a repolarization signal for computing T-wave alternans, it may be useful to exclude two consecutive cardiac cycles to preserve the pattern of alternans, even if only one of two consecutive cardiac cycles is found to have an invalid T-wave.

As consistent with other embodiments described herein, a denoised cardiac repolarization signal is used to assess repolarization abnormality using one or more of T-wave alternans, T-wave variability, T-wave morphology changes, and T-wave complexity. T-wave alternans (TWA) are defined as beat-to-beat fluctuations in amplitude, polarity, or shape of a T-wave. In one embodiment T-wave alternans can be measured as spectral energy at one-half the heart rate. In another embodiment, a time-based metric is calculated by separating the cardiac cycles into even and odd beats. A weighted average of odd and even beats can then be calculated and TWA is quantified as the difference between the averaged odd and even beats. In another embodiment, a time-frequency based metric of TWA is calculated by performing a stationary wavelet periodogram of the repolarization signal. The TWA are quantified as a ratio of power at adjacent wavelet scales.

In other embodiments, repolarization abnormalities are characterized by evaluating aspects of T-wave variability. In one embodiment, feature points of valid denoised T-waves are identified using the emphasis signal and variance of the T-wave or T-wave emphasis signal at these feature points is computed. These feature points may include the positive peak amplitude, negative peak amplitude, amplitude approximately midway in time between onset and peak, and amplitude approximately midway in time between peak and offset. In another embodiment, variability and trends in time of the feature points relative to, for example T-wave onset, is analyzed as a means of characterizing repolarization abnormalities and changes. In another embodiment, valid denoised T-waves are segmented into equal intervals (e.g., first one-fourth, second one-fourth, etc.) and area or amplitude variability of each segment is computed for an ECG segment consisting of several (e.g., 10 to 500) cardiac cycles.

Changes in T-wave morphology can be indicative of reduced repolarization reserve leading to a proarrhythmic scenario. In one embodiment, T-wave morphology is quantified using extracted feature points of the emphasis signal, as described above, and changes in T-wave morphology metric are tracked over time (e.g., hours, days, weeks, or months). In one embodiment, at least one of beat-to-beat variability metrics and multiscale entropy of T-wave parameters can be computed and trended in time. Unusual patterns in T-wave morphology can be used as a marker of impending arrhythmia. In one embodiment, these patterns can be detected as changes in a T-wave complexity metric, with the metric computed as described later.

Various embodiments are directed to computing and evaluating an emphasis signal for detecting Q-wave onset and T-wave offset points. In an example embodiment, and referring to FIG. 4, an ECG signal 401 is decomposed 402 into subcomponents in a second domain of higher dimension than the first domain. The subcomponents are denoised 403 by identifying and excluding those subcomponents that are primarily associated with noise at a particular point in time. An emphasis signal for a signal wave is computed 404 by combining one or more subcomponents that are primarily associated with the signal wave and the emphasis signal is evaluated 405 for identifying transitions and features within the ECG. Identifying Q-wave onset and T-wave offset, for example, involves creating an emphasis signal for each signal wave by combining the associated subcomponents and then identifying appropriate peaks, valleys, and baseline points of the emphasis signal.

Figure 4A:
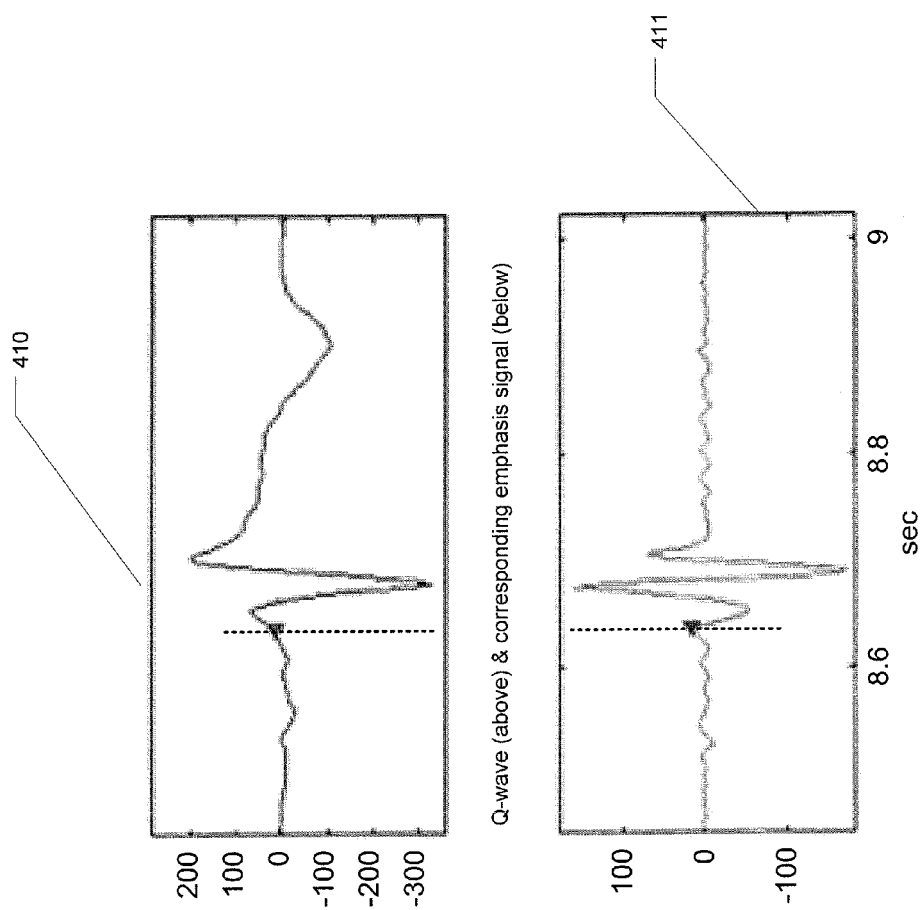
Figure 4B:
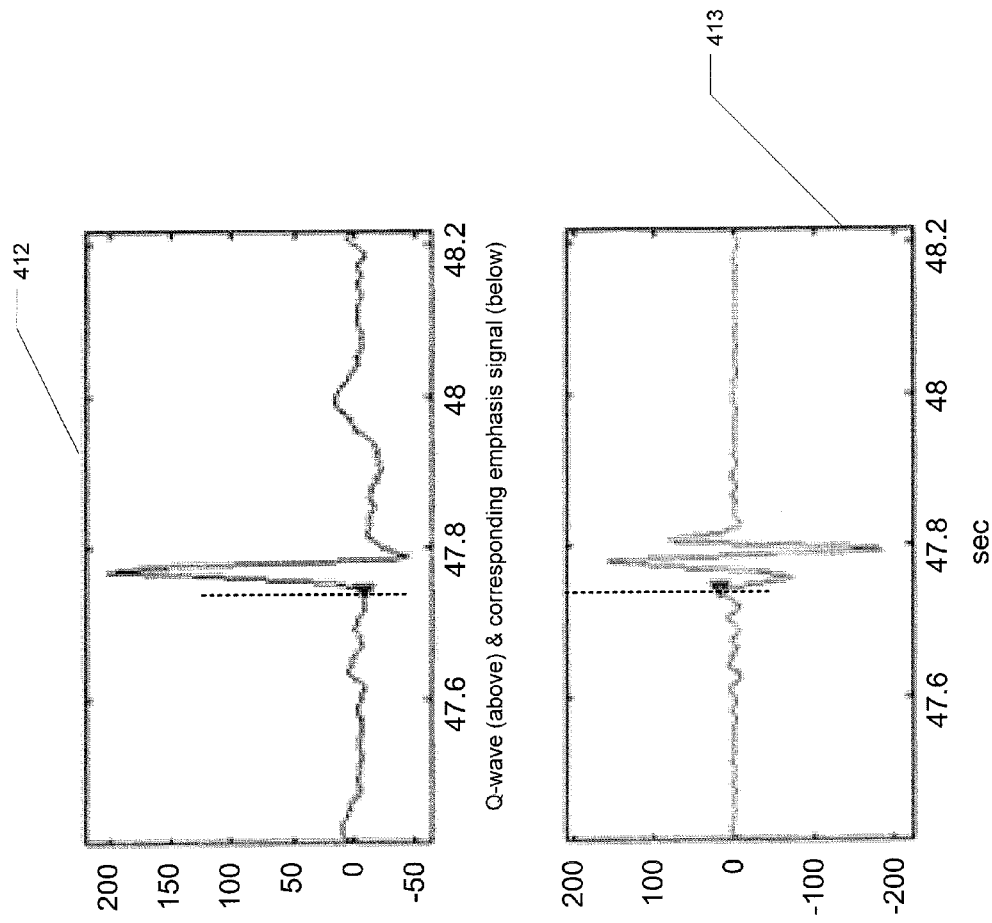
Figure 4C:
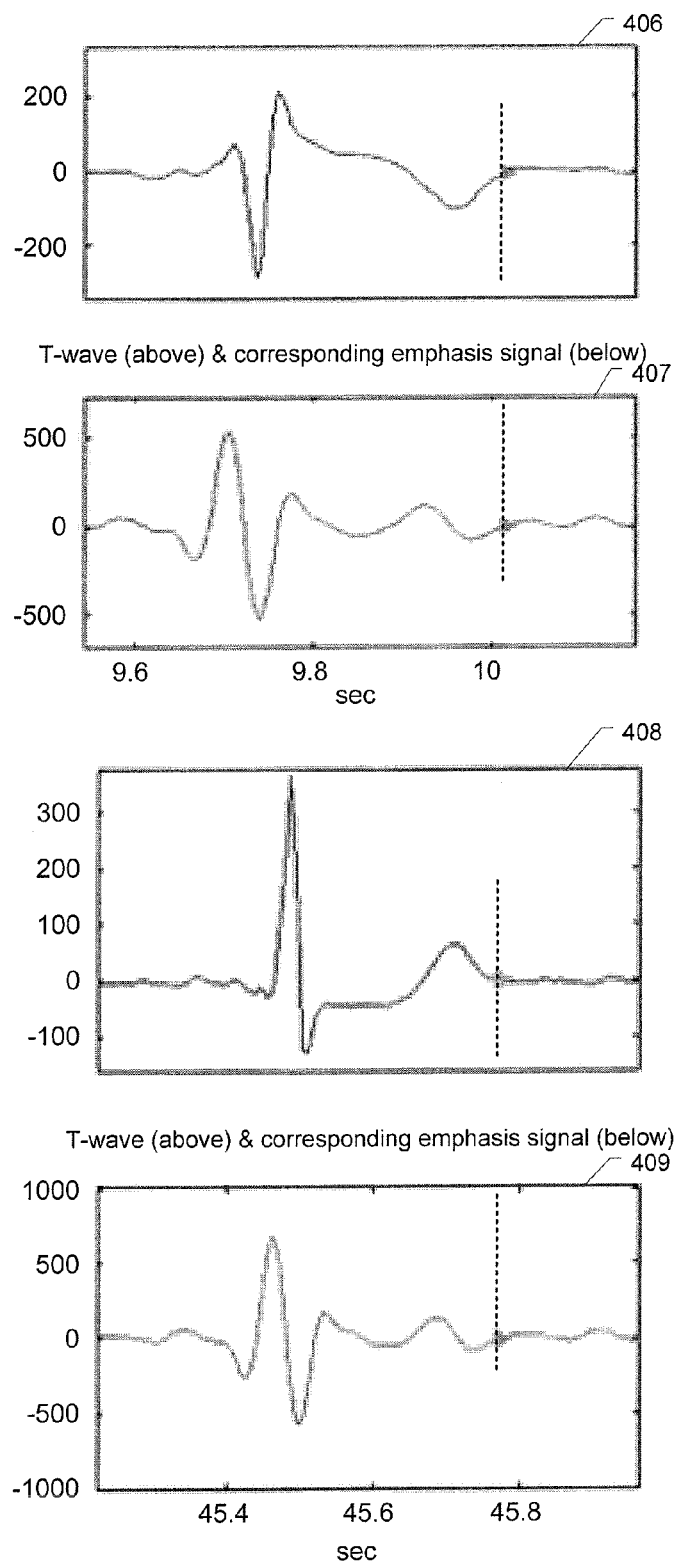

In connection with various embodiments, the specific subcomponents associated with each signal wave (e.g., T-wave and Q-wave) are used in accordance with the species, sampling rate, and decomposition method used. For example, if decomposition is achieved using a discrete wavelet-related transform, the species is a human being, and the ECG is sampled at 250 Hz, the T-wave associated subcomponents correspond to wavelet scales $2^4$ and $2^5$. The emphasis signal that is computed from one or two of these scales is proportional to the derivative of the filtered version of the T-wave. Referring to FIG. 4C, two different T-wave morphologies and the corresponding T-wave emphasis signals are shown with T-wave offset marked by a vertical dashed line on both the ECGs and the emphasis signals. The T-wave emphasis signal is evaluated to identify T-wave offset based upon an evaluation of the pattern of peaks, valleys, and zero crossings. As can be seen in FIG. 4C, T-wave offset is identified as the first baseline point following the last significant peak or valley in the T-wave emphasis signal.

The Q-wave emphasis signal is evaluated using similar techniques. In one embodiment, decomposition subcomponents associated with the Q-wave correspond to wavelet scales $2^2$ through $2^4$ assuming a human ECG sampled at 250 Hz and decomposed using a discrete wavelet-related transform. These subcomponents are combined to create an emphasis signal that is evaluated beginning at the peak of the R-wave, going backward in time. Referring to FIGS. 4A-4B, two different QRS morphologies and the corresponding Q-wave emphasis signals are shown. As can be seen in the Figures, Q-wave onset is identified (as shown by the vertical dashed line) as the first baseline point prior to the first significant peak or valley of the emphasis signal prior to the location of the R-wave peak.

In some embodiments, noise is removed from the subcomponents in order to create a less noisy emphasis signal. Reduction of noise in the emphasis signal facilitates more accurate and consistent detection of peaks, valleys, and baseline points during the process of identifying T-wave offset, T-wave onset, Q-wave onset, and the R-wave. One denoising approach involves identifying subcomponents that are primarily associated with noise so that they can be eliminated during reconstruction of the signal. This is accomplished by using one or a combination of principal component analysis (PCA), independent component analysis (ICA), periodic component analysis (πCA) and spatially selective filtering (SSF).

The PCA technique can be applied to multi-lead ECG and uses information on subcomponent covariance to orthogonalize subcomponents. The orthogonalized subcomponents with low signal power are often associated with noise and can be removed to achieve denoising. PCA can be used as a preliminary step prior to applying an ICA technique to multi-lead ECG. The ICA technique can further be used to separate signal and noise sources as a solution of an optimization problem that maximizes independence between them. The πCA technique can be applied to both single lead and multi-lead ECG and computes and jointly diagonalizes covariance and autocorrelation matrices of subcomponents to separate them based on their periodicity or quasi-periodicity [12, 13]. The πCA technique extracts most periodic subcomponents corresponding to ECG rhythm and, since noise is not generally periodic, it is left behind.

SSF techniques can be used on either multi-lead or single lead ECG and detect signal-related features and pass them across the subcomponents while blocking features inherent to noise. The technique is based upon the differences in noise and signal distributions across decomposition levels. In one embodiment, spatially selective filtering is facilitated by a decomposition whereby signal energy is concentrated in a small number of large subcomponent coefficients while noise is spread out across many decomposition levels and is represented by small coefficients. In another embodiment, spatially selective filtering exploits the fact that most noise subcomponents are confined to levels that represent high frequencies. In this embodiment the locations of signal features are identified by examining subcomponents corresponding to lower frequency. The subcomponents associated with high frequency are then zeroed except those locations where the signal features were identified.

Computed QT intervals can be used to calculate metrics associated with reduced repolarization reserve and potential proarrhythmic scenario. Such metrics include:

Mean prolongation or reduction of QT interval
Standard Deviation of QT from N consecutive beats (SD)
Root mean square of N successive differences of QT intervals (RMSSD)
Standard deviation of N successive differences of QT intervals (SDSD)
Beat-to-beat variability of successive differences measured as $2*SD^2-1/2*SDSD^2$.
Short-term variability of QT interval, $$STV_D = \sum_{i=1}^{N} |D_{n+1} - D_n| / [N\sqrt{2}],$$

where $D_n$—is a QT interval from n-th beat
Long-term variability of QT interval:

$$LTV_D = \sum_{i=1}^{N} |D_{n+1} + D_n - 2D_{mean}| / [N\sqrt{2}],$$

where $D_n$—is a QT interval from n-th beat

In another embodiment nonlinear measures of complexity of repolarization dynamic such as multiscale entropy [21] are computed to measure variability beyond a single beat lag. In another embodiment, changes in QT/RR hysteresis [22] are trended over time.

Figure 5:
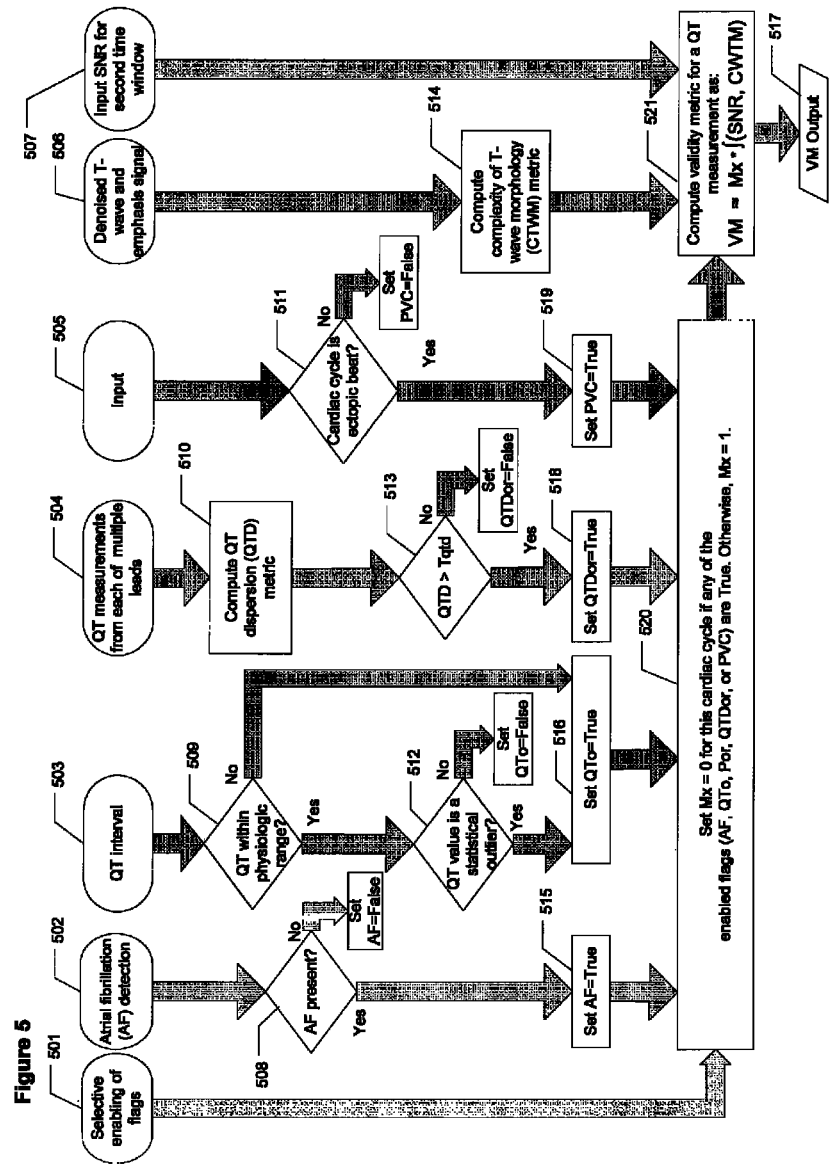
FIG. 5 provides an example data flow and decision diagram for computing a validity metric, consistent with one or more example embodiments of the present invention.

In another example embodiment, and referring to FIG. 5, a validity metric (VM) is computed for assessing the validity of a QT interval measurement or a repolarization wave identified in a cardiac cycle. In one embodiment, and referring to FIG. 5, VM is computed on a cardiac cycle-by-cycle basis. FIG. 5 shows several inputs that can be useful in computing VM. These inputs include: a) a signal 502 indicating whether atrial fibrillation (AF) is present in the cardiac cycle, b) QT interval 503 for the cardiac cycle, c) whether the cardiac cycle is an ectopic beat such as a premature ventricular contraction (PVC), d) degree of complexity of the T-wave morphology, and e) signal-to-noise ratio (SNR) for the second time window. When the ECG being evaluated is a multi-lead ECG, it can also be useful to employ a measure of the degree of dispersion of QT (QTD) measurements between leads [23] when computing validity. In one embodiment, each of these inputs can be selectively enabled in control input 501. For example, in some embodiments the flag is disabled for ectopic beats such that QT values obtained from such cardiac cycles are considered valid. This can be useful when QT variability is computed as an indicator of proarrhythmogenicity [18]. In other embodiments, such as when a repolarization wave is being isolated to construct a repolarization signal time series, the PVC flag is enabled so that ectopic beats are excluded from the repolarization time series.

Inputs 502, 503, 504, and 505 are each processed in a manner that if one of these input signals meets certain criteria and the flag corresponding to the input is enabled, the multiplier Mx is set to 0 in process 520. The absence of one of the input signals 502 to 505 forces Mx=0, Mx=1 for the cardiac cycle. Mx is passed from process 520 to process 521 and is used as a multiplicand in the computation of VM. Hence if Mx=0, then VM=0 for that cardiac cycle. Hence, if Mx=0 a QT interval measurement or repolarization wave for a cardiac cycle would be deemed invalid regardless of input SNR 507.

In some embodiments, input 502 contains information as to whether the cardiac cycle is part of an AF episode. If the cardiac cycle is determined to be part of an AF episode in decision process 508, the flag AF is set to a value True in process 515. Otherwise flag AF=False. If the AF Flag is enabled by input 501 and the AF Flag is True, then process 520 will set Mx=0. Modulating the value of VM according to the presence or absence of AF can be useful because, during AF, P (or F) waves may occur during the T-wave resulting in blurred T-wave offset or onset and distorted T-wave morphology.

In some embodiments, the value of QT for the cardiac cycle is contained in input 503. In decision process 509, the QT value is compared to a predetermined range corresponding to the outer bounds of the physiological limits of the subject species. If the QT value is outside this range, then the QTo Flag is set to True. If the QT value is within physiological range, then it is evaluated in decision process 512 to determine if it is a statistical outlier (e.g., outside of a statistical range). In process 512, the QT value is compared to a range defining normal and outlier values. In one embodiment, an outlier is defined as mean or median+/−3 standard deviations of QT interval for beats in a predefined time window. In some embodiments a QT interval is evaluated relative to a predefined limit to avoid discarding valid QT interval values when variability is low.

In some embodiments, in which the ECG signal is from a multi-lead ECG, QT measurements for the cardiac cycle from each of the various leads are input in 504. QT dispersion is computed in process 510 (e.g., using methods described in reference 31 below). A high value of QTD can indicate that there are errors in computing QT interval in one or more leads due to noise, artifact, or algorithm error [23] and hence the validity of the QT measurement may be questionable. In decision process 513, QTD is compared to a threshold Tqtd. If QTD exceeds Tqtd, the flag QTDor is set to True. If QTD is <Tqtd, then the flag QTDor is set to False. If the flag QTDor is enabled and is True, then the multiplier Mx is set to 0 in process 520.

In some embodiments, input 505 contains information as to the character of the cardiac cycle. This information is evaluated in decision process 511 and, if the cardiac cycle is identified as containing an ectopic beat, the flag PVC is set to True in process 519. If the beat is determined not to be an ectopic beat in decision process 511, then flag PVC is set to False. If flag PVC is enabled and is True, then Mx is set to 0 in process 520.

In some embodiments the T-wave and emphasis signal for the cardiac cycle are input in process 506. A measure of the complexity of T-wave morphology (CTWM) is computed in process 514. In one embodiment CTVVM is computed as the number of significant peaks and valleys in the T-wave emphasis signal during the time from T-wave onset to T-wave offset. In another embodiment relative locations of the emphasis signal peaks and valleys are included in the computation of the CTWM metric. If the T-wave is highly complex, as is the case for a multiphasic T-wave, then the validity metric is reduced to reflect that a U-wave may be present and thus accuracy of identification of the T-wave offset point may be compromised.

In some embodiments, a metric of signal energy relative to noise energy for the second time window (218 for T-wave offset VM and 317 for repolarization VM) is input in 507 for use in computing VM. In some embodiments this metric is SNR and is computed as described previously. In one embodiment, SNR for the second time window is computed in processes 218 and 304 as the energy contained in the subcomponents primarily associated with the T-wave and noise energy is computed from the energy contained in the residual subcomponents. In some embodiments, process 521 computes VM as a function of SNR and CTWM multiplied by Mx, where Mx is computed in process 520 and Mx=0 or 1. In some embodiments, VM is maintained at zero for a predetermined number of subsequent cardiac cycles following an ectopic beat to account for hysteresis effects in QT interval that can occur following an arrhythmic beat. In some embodiments VM is evaluated and, if found to be below a predetermined threshold Td, the QT measurement for that cardiac cycle is considered invalid and is discarded. Likewise, if VM is >than a predetermined threshold Tg then the QT measurement is considered valid. In some embodiments, if VM has a value between Tg and Td it is considered uncertain. QT measurements for cardiac cycles where Tg>VM>Td may be reviewed by a trained person to manually assign a T-wave offset point.

In some embodiments QRS duration is measured using the Q-onset and QRS offset fiducial points detected as described herein. As part of measuring QRS duration, the signal energy relative to noise energy may be measured in one or more windows within which the presence of noise can impact the accuracy of Q-onset and QRS offset detection in a manner similar to that described for T-wave offset.

Various embodiments are directed to adjusting QT measurements to facilitate and/or improve the accuracy of resulting data. In accordance with an example embodiment, and referring to FIGS. 6-6C, measurements of T-wave offset are adjusted using a technique that employs an evaluation of T-wave morphology in order to further improve the accuracy and consistency of T-wave offset detection results. Improved consistency in T-wave offset measurement can be useful because it leads to reduced measurement variability which can translate into a reduction in sample size in various research studies, including those that employ QT measurements to investigate proarrhythmic potential of drugs under development [24]. The embodiments described here may be useful for improving the accuracy and consistency of identifying T-wave offset for computing a QT interval parameter or for improving the accuracy and consistency of identifying T-wave offset and T-wave onset for extracting a repolarization signal. A similar approach may also be useful for improving the accuracy of other feature points such as Q-wave and P-wave onset.

This approach is based upon the assumption that normal physiologic variability in T-wave offset relative to cardiac depolarization is small over a period of a few respiratory cycles, providing that T-wave morphology is consistent over that time period. However, residual noise, inappropriate high pass filter settings [25] or baseline fluctuations can bias detection of T-wave offset. Such biases can accumulate, resulting in variability of QT interval measurements that is much greater than normal physiologic variability. This embodiment is useful in reducing the impact of these biases on T-wave offset identification.

Figure 6A:
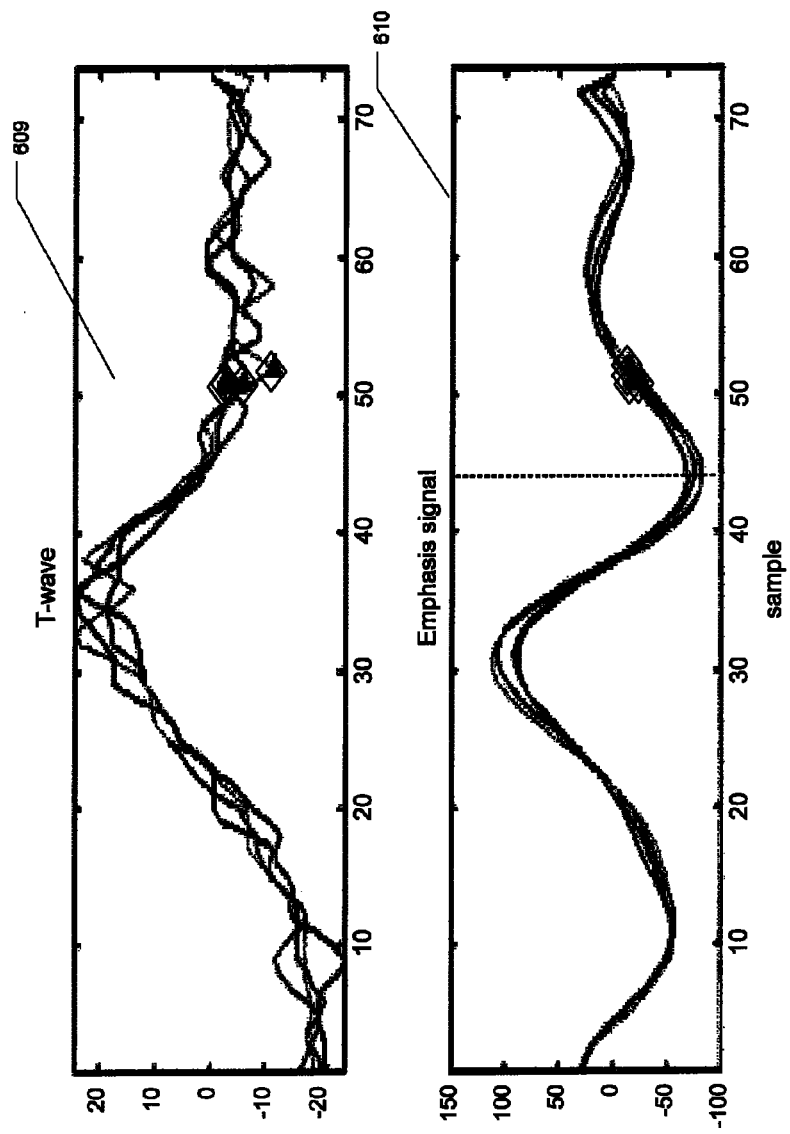
Figure 6B:
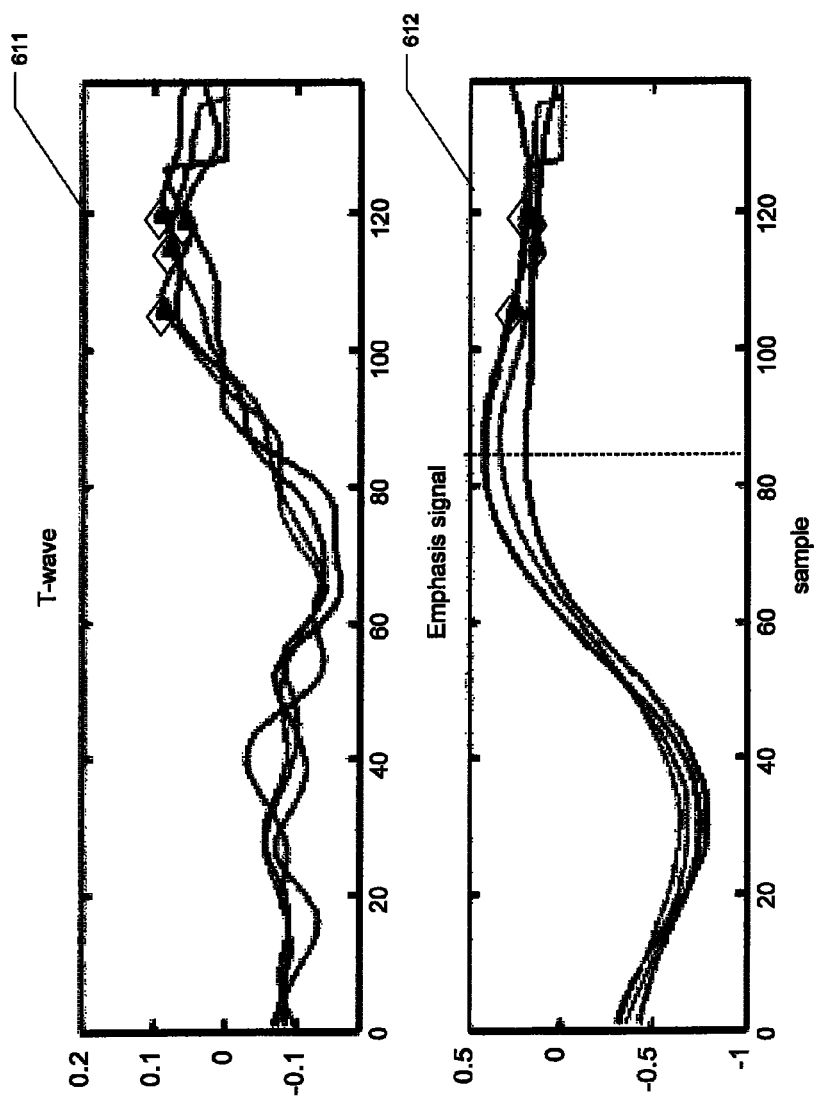

In this embodiment, and referring to FIG. 6, input ECG 601 is evaluated in process 602 to identify T-wave offset as described previously. The emphasis signal is computed in process 603, also using techniques described previously, and is evaluated in process 604 to identify T-waves with similar morphology characteristics. Morphology characteristics of each T-wave are evaluated and T-waves with common morphology 3*n* characteristics are assigned to a cluster in process 605. In process 606, T-waves assigned to a cluster are aligned in time around a common feature point of the T-wave emphasis signal, referred to as an alignment point. In one embodiment, the alignment of T-waves in process 606 is performed in a manner that preserves the time difference between the alignment point and the initially derived T-wave offset point. Because QT variability can be caused by changes in the QRS duration (e.g., as often occurs as a result of respiratory modulation), it can be useful to make any adjustment to T-wave offset relative to a reference point within the T-wave. In one embodiment, a composite value for T-wave offset is computed following alignment of T-waves within a cluster. The composite value can be computed as the median, mean or weighted mean of the T-wave offset points of the aligned T-waves in the cluster. The initially derived T-wave offset points for T-waves in the cluster are then adjusted to match the composite value. In another embodiment, T-wave offset points in the cluster are adjusted to match the computed mean value. In another embodiment, computing the composite value for the cluster involves removing statistical outliers (e.g., T-wave offset times a predefined multiple of S.D. of mean) prior to computing a mean, following alignment of T-waves in process 606, a composite T-wave offset value is computed in process 607 by combining the offset points of the aligned T-waves. In process 608, T-wave offset values for each cardiac cycle in the cluster are adjusted by matching T-wave offset points to the composite values computed in 608.

In another embodiment the T-waves in a cluster can be averaged to compute a template automatically. Template matching techniques, such as cross-correlation, can then be used to correct computed T-wave onset and offset.

In one embodiment, T-wave morphology is evaluated by analyzing the time and amplitude of significant peaks, valleys, and zero crossings (e.g., fiducial points) of the emphasis and the denoised signals. In one embodiment, T-waves having the same number and similar amplitude of fiducial points as well as similar time between the fiducial points are assigned to a common cluster. In another embodiment the number and either time or the amplitude of the fiducial points are used for morphology classification.

In another embodiment, the time scale of a T-wave is compressed or expanded in order to allow it to match the criteria of a morphology cluster for reducing the number of clusters. Creating this modified T-wave facilitates clustering based upon shape of the T-wave rather than time scale. The T-wave offset point correction for the modified T-wave is adjusted back in time in proportion to the change in time scale made when creating the modified T-wave.

Figure 6C:
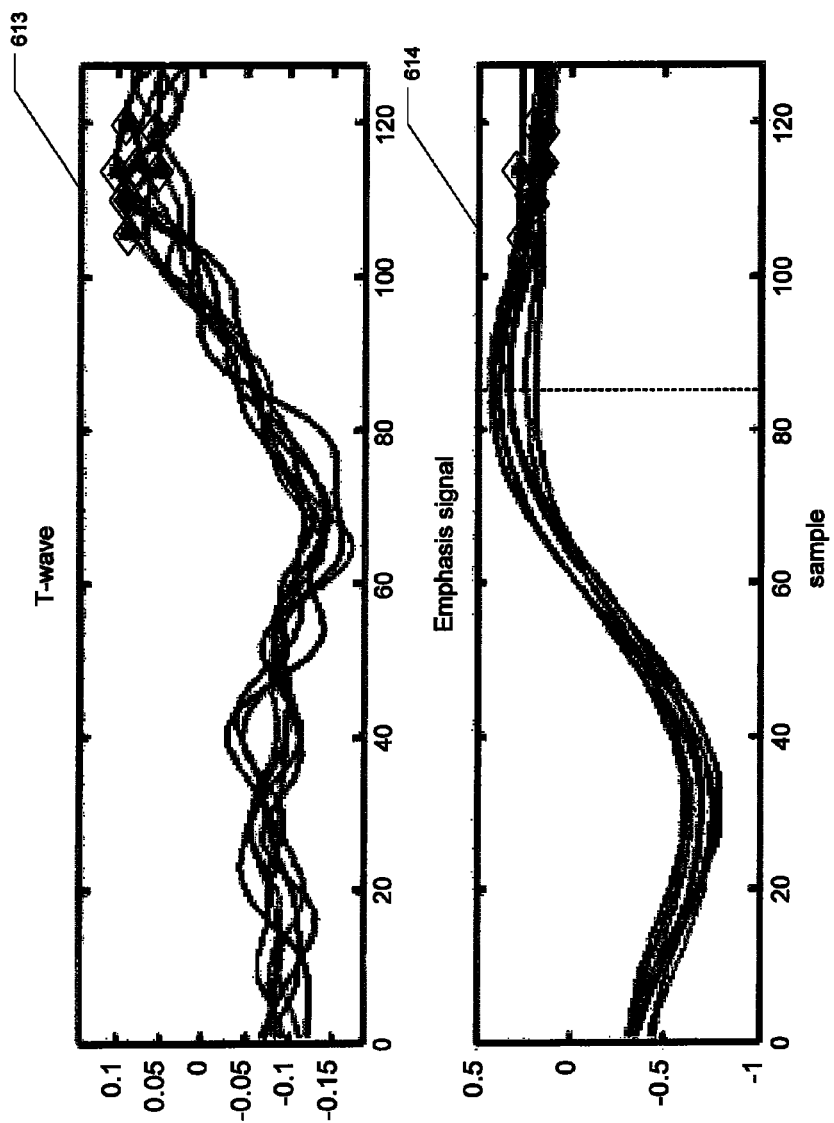

Referring to FIGS. 6-6C, relative to respective embodiments, examples are presented for noisy human T-waves in 609 and derived emphasis signals in 610 and for canine T-waves and derived emphasis signals 611 through 614. The rhombus symbols denote the point of detection of T-wave offset for each of the T-waves shown. In 609, T-waves of similar morphology have been identified as belonging to a particular classification by examining peaks and valleys of the emphasis signal. The emphasis signals shown in 610, computed from denoised subcomponents as described earlier, provides a useful tool for evaluating the classification of a T-wave since it contains less noise and provides for a more precise and consistent location of features. The T-waves in a cluster can be aligned by the location of the first significant peak or valley of the emphasis signal. The alignment points computed from the emphasis signals of this cluster are shown as a vertical dashed line in 610.

An example, shown in 609 and 610, reveals that one of the T-wave offset points (indicated by the right-bottom rhombus in T-wave cluster in 609) is displaced from the others in the cluster by about two sample points due to residual noise. The identified T-wave offset can be repositioned to match mean or median T-wave offsets in the cluster. The examples of 611 (T-waves) and 612 (derived emphasis signals) demonstrate this embodiment as applied to a canine ECG. In 611 and 612 the T-waves and emphasis signals are shown aligned around the first significant peak or valley of the emphasis signal (indicated by the vertical dashed line in 612). As for 611, the majority of T-wave offset points coincide, but one T-wave offset (left-most rhombus) differs from the others by about 5 sample points due to noise. This T-wave offset can be repositioned to match the mean or median of the cluster to ensure consistency of T-wave offset measurement. Alternately, this initially derived T-wave offset point would be identified as an outlier and removed from computation of the composite value.

Some embodiments may use more or less stringent criteria to evaluate the morphology characteristics for assigning a T-wave to a cluster. An example of a modified embodiment is provided in 613 and 614 whereby a more relaxed definition of the morphology cluster is used. The criteria used to determine if a T-wave is assigned to a cluster has been relaxed to allow a +/−1 sample point difference in the distance between the fiducial points of the emphasis signal, whereas the examples of 609 to 612 require that fiducial points match exactly. The relaxed inclusion criteria results in a smaller number of clusters used for T-wave offset correction, with a larger number of T-waves in each cluster. As is seen from 613 (T-waves) and 614 (emphasis signals) the T-wave offset points are more scattered in time. In one embodiment the initially derived T-wave offsets are replaced by a mean or median of T-wave offsets in the cluster. In an alternate embodiment, statistical outliers are eliminated from computation of the T-wave offset point.

The embodiments described here for measuring and analyzing QT interval and other metrics of cardiac repolarization activity may be implemented in a variety of platforms, such as those including a computer, processor and/or related circuitry. In one embodiment, a microprocessor (such as an Intel Pentium or Core microprocessors) or microcontroller (such as the Texas Instruments MSP 430 microcontroller) is configured (e.g., programmed) to implement one or more embodiments, such as those shown in and/or described in connection with the figures. In other embodiments a mainframe computer or a state machine such as may be implemented on silicon using a hardware description language such as VHDL is used to implement one or more embodiments. Still other embodiments are directed to the implementation of different aspects of the embodiments described herein, such as certain computing steps and/or the computation of certain values (e.g., a denoised signal), whereas other aspects are implemented using different steps using other processors/machines and/or at disparate locations, with resulting data communicated appropriately (e.g., via the Internet). Accordingly, some embodiments are directed to certain post-processing in which certain computations have been made, as may be relevant, for example, to the computation of a QT interval and related characteristics using a provided denoised signal. Certain embodiments involve combining the measurement of QT interval and other metrics of repolarization activity with other ECG analysis functions such as detection of atrial and ventricular arrhythmias and measurement of characteristics such as QRS duration and PR interval.

Some embodiments of the present invention are implemented in a battery or passively powered device that is worn by or implanted within a human or animal subject. Referring to FIG. 7, aspects of the present invention can be implemented within subject device 704A and 704B while others can be implemented in data review system 707. In FIG. 7, it is anticipated that multiple subjects are monitored and hence there are multiple subject devices (704A and 704B) and multiple base stations (705A and 705B). In one embodiment, input ECG 701 is amplified and filtered to remove out-of-band noise in 702. The conditioned signal from 702 is digitized by microcontroller 703. Microcontroller 703 and related functional elements contain a processor, memory, communications module, and other functions necessary to acquire, process, and control operation of subject devices 704A and 704B. In some embodiments, microcontroller (embedded system) 703 processes the conditioned ECG signal to derive QT interval measurements and repolarization signals and communicates the information derived from the ECG via a communication module. Information is received by base stations 705A and 705B and is forwarded to data review system 707 via telecom or data network 706.

The computer instructions required to perform the computing operations of the present invention are programmed (e.g., optimized) using integer or fixed point arithmetic and lifting or B-spline implementation [26, 27] of the signal decomposition transform in order to minimize the number of clock cycles or machine states required and hence minimize power consumption. The resulting code can then be implemented, for example, in an embedded system 703 capable of operating for an extended period of time on power supplied by a small battery. In such an embodiment, a portion of the computations required to analyze repolarization activity and extract other information on heart rhythms may be implemented within subject device 704A and 704B while others may be implemented in data review system 707. In another embodiment, the subject device only records the ECG of the subject and the ECG recording is processed off line on data review system 707. Data review system 707 may include a review function that facilitates human review of ECGs that were classified as uncertain by the algorithm.

Figure 9:
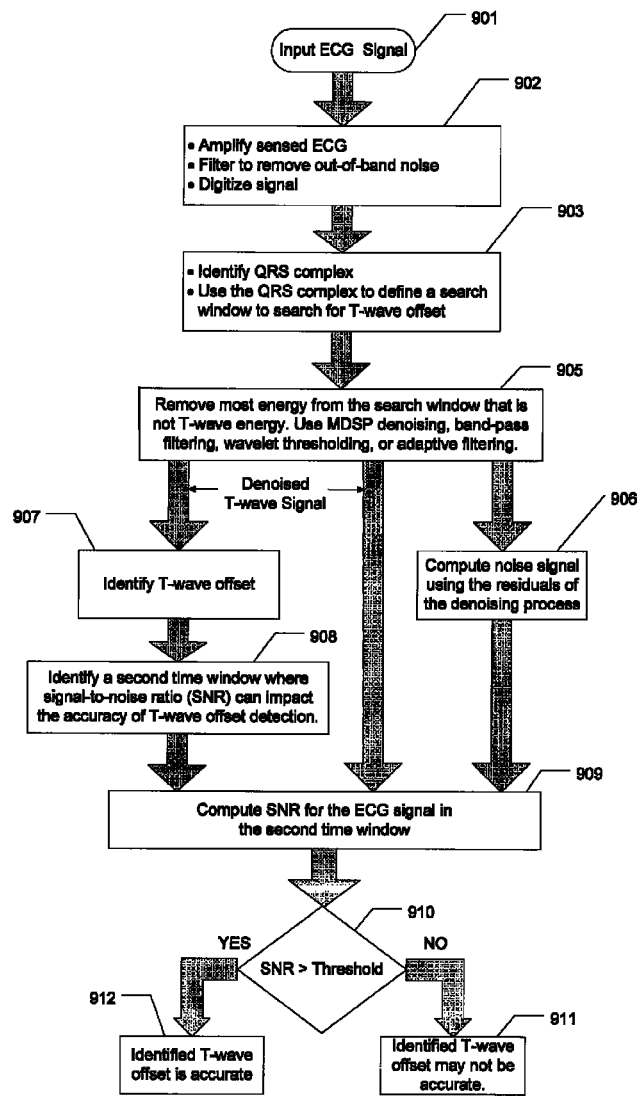
FIG. 9 shows another flow diagram involving the processing of an ECG signal to provide a T-wave offset, in accordance with another example embodiment of the present invention.

In another example embodiment, and referring to FIG. 9, a sensed ECG signal 901 is received and processed to provide a T-wave offset. The received signal is amplified and filtered in 902 to remove signal content that is outside the bandwidth of the ECG. The filter employed in 902 may include one of a number of filters, such as a multi-pole Butterworth filter. For human ECGs, the lower and upper (−3 dB) filter cutoff points can be 0.05 and 100 Hz, respectively. The amplified and filtered signal is also digitized in 902 for processing by a computing element such as a microprocessor, signal processing element, or state machine where steps 903 through 912 are implemented via software, firmware, or hardware description language. In step 903, the QRS complex is identified and the location of the QRS complex is used to define a search window within which to search for T-wave offset, using one or more approaches such as those described herein.

The ECG signal is then filtered and/or denoised in step 905 to remove the energy outside the frequency components of the T-wave. Step 905 is accomplished by one of MDSP denoising, band-pass filtering, wavelet thresholding [30], and adaptive filtering. The output denoised T-wave is processed to identify T-wave offset in step 907, and a noise signal is computed in step 906 as the residual of the T-wave denoising process. In one embodiment, the noise signal can be computed in 906 by subtracting the denoised T-wave signal computed in step 905 from the digitized ECG signal produced in step 902.

The T-wave offset point identified in step 907 is used in step 908 to identify a second time window. This second time window includes a portion of the T-wave where the presence of noise can impact the accuracy of T-wave offset detection and the considerations for duration and location of this time window are similar to those used to define second time windows 218 and 317. In some embodiments this time window includes the T-wave offset point and may also include a range of time preceding the T-wave offset point and a range of time following the T-wave offset point. In some embodiments the second time window begins at the first significant peak of the T-wave, where the first significant peak is defined as either the highest amplitude positive or negative peak or the first peak preceding the highest amplitude peak that is greater than 50% of the amplitude of the highest peak. In some embodiments the second time window begins at the highest positive or negative T-wave peak. In other embodiments the duration of the second time window is set to about ⅓ of the duration of the nominal QT interval for the species for which QT interval is being measured. In this embodiment the second window may be positioned so that it terminates at a point corresponding to a distance of about 10% of the nominal QT interval after the T-wave offset point, with about 90% of the duration of the second window preceding the T-wave offset point. In another embodiment, the second window has a fixed duration, such as about 50 msec, and is roughly centered on the T-wave offset point.

In step 909 a noise characteristic is computed for the second time window for use in determining whether the T-wave offset point is accurate and/or valid. In one embodiment, the noise characteristic is a signal-to-noise ratio computed using the denoised T-wave and noise signals present in the second time window. In another embodiment, the noise signal present in the second time window is used to compute noise energy present in the second time window. In another embodiment, the noise signal present in the second time window is used to compute a standard deviation of the noise in the second time window. In another embodiment, the noise signal in the second time window is used to compute a zero crossing density in the second time window. In yet another embodiment, a metric of noise amplitude is computed using an envelope. This can be accomplished by applying a Hilbert transform to the noise signal in the second time window and computing an absolute value of the transform output. The absolute value output is then low-pass filtered to compute an envelope of the noise signal.

In step 910, the noise characteristic computed in step 909 is compared to a threshold. In an embodiment in which the noise characteristic is computed as SNR, SNR is compared to a threshold and, if >the threshold, the identified T-wave offset point is considered to be accurate and valid in 912. If it is less than the threshold, it is identified as possibly inaccurate in 911 and may not be included in subsequent analysis. In one embodiment, the threshold evaluated in 910 is a validity metric (VM). In one embodiment, VM is computed as described previously and, referring to FIG. 5, SNR computed in 909 corresponds to input 507.

For general information regarding a variety of fields that may relate to one or more embodiments of the present invention, and for specific information regarding the application of one or more such embodiments, reference may be made to the following documents, which are fully incorporated herein by reference. Various ones of these references are further cited above via corresponding numerals, and may be implemented as such.

1. K. R. Rao and P. Yip, *Discrete Cosine Transform: Algorithms, Advantages, Applications* San Diego, Calif.: Academic, 1990.
2. Mallat, S. G., and Zhang, Z., Matching Pursuits with Time-Frequency Dictionaries, IEEE TSP(41), No. 12, December 1993, pp. 3397-3415.
3. Vaidyanathan, Multirate Systems and Filter Banks, Prentice Hall, 1993
4. J. Woods. Subband Coding, Kluwer Academic Press, 1990.
5. K. S. Ball, L. Sirovich, L. R. Keefe, Dynamical eigenfunction decomposition of turbulent channel flow. International Journal for Numerical Methods in Fluids Volume 12, Issue 6, Date: 5 Apr. 1991, Pages: 585-604
6. Lipponen J, Tarvainen M, Laitinen T, Lyyra-Laitinen T, Karjalainen P. A Principal Component Regression Approach for Estimation of Ventricular Repolarization Characteristics. IEEE Trans Biomed Eng. 2010 vol. 57 no. 5 pp. 1062-1069
7. H. Li, R. Li, F. Wang. Multiresolution Subband Blind Source Separation: Models and Methods. Journal of Computers, Vol 4, No 7 (2009), 681-688
8. Martínez J P, Almeida R, Olmos S, Rocha A P, Laguna P. A wavelet-based ECG delineator: evaluation on standard databases. IEEE Trans Biomed Eng. 2004 April; 51(4): 570-81.
9. L. Smith A tutorial on Principal Components Analysis, http://users.ecs.soton.ac.uk/hbr03r/pa037042.pdf
10. Aminghafari, M.; Cheze, N.; Poggi, J-M. (2006), "Multivariate de-noising using wavelets and principal component analysis," *Computational Statistics & Data Analysis*, 50, pp. 2381-2398
11. P. Comon, "Independent component analysis, a new concept?," Signal Process. Special Issue on Higher Order Statistics, vol. 36, no. 3, pp. 287-314, 1994..
12. L. K. Saul and J. B. Allen, "Periodic component analysis: An eigenvalue method for representing periodic structure in speech," in NIPS, [Online]. 2000, pp. 807-813. Available: http://www.cs.cmu.edu/Groups/NIPS/00papers-pub-on-web/SaulAllen.pdf
13. R Sameni, et. al. Multichannel electrocardiogram decomposition using periodic component analysis. IEEE Transactions on Biomedical Engineering, 2008 vol 55, no 8 pp 1935-1940
14. Mallat, S. and Zhong, S. 1992. Characterization of Signals from Multiscale Edges. IEEE Trans. Pattern Anal. Mach. Intell. 14, 7 (July 1992),
15. Mallat, S. G., Hwang, W. L., Singularity Detection and Processing with Wavelets, IEEE Transactions on Information Technology (38), 1991, pp. 617-643.
16. Xu, Yansun, et. al. Wavelet transform domain filters: a spatially selective noise filtration technique, IEEE transactions on image processing 1994, vol. 3, no6, pp. 747-758
17. B. U. Kohler, C. Hennig, R. Orglmeister. The principles of software QRS detection. IEEE Engineering in Medicine and Biology Magazine, Vol. 21, No. 1. (2002), pp. 42-57.
18. Attila S. Farkas. et. al. Biomarkers and endogenous determinants of dofetilide-induced torsades de pointes in al-adrenoceptor-stimulated, anaesthetized rabbits. British Journal of Pharmacology. Vol 161, Issue 7, pp 1477-1495, December 2010
19. Thomsen, M. B., Verduyn, S. C., Stengl, M., Beekman, J. D., de Pater, G., van Opstal, J., et al. (2004). Increased short-term variability of repolarization predicts d-sotalolinduced torsade de pointes in dogs. Circulation, 110, 2453-2459.
20. M. Brennan, M. Palaniswami, and P. Kamen. Do Existing Measures of Poincaré Plot Geometry Reflect Nonlinear Features of Heart Rate Variability? IEEE Transactions On Biomedical Engineering, Vol. 48, No. 11, November 2001
21. Madalena Costa. et. al. Multiscale entropy analysis of biological signals. Physical Review E 71, 021906 s2005d.
22. M. Malik, K. Hnatkova, T. Novotny, G Schmidt Subject-specific profiles of QT/RR hysteresis. Am J Physiol Heart Circ Physiol 295:H2356-H2363, 2008
23. Malik M, Batchvarov VN. Measurement, interpretation and clinical potential of QT dispersion. J Am Coll Cardiol. 2000 Nov. 15; 36(6):1749-66.
24. Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. 2004 December; 27(12):1659-69.
25. Hamlin R L. Non-drug-related electrocardiographic features in animal models in safety pharmacology. J Pharmacol Toxicol Methods. 2005 July-August; 52(1): 60-76.
26. K. G. Oweiss, A. Mason, Y. Suhail, A. M. Kamboh and K. E. Thomson "A scalable wavelet transform VLSI architecture for real-time signal processing in high-density intra-cortical implants", IEEE Trans. Circuits Syst. I, vol. 54, pp. 1266 2007.
27. W. Sweldens. The lifting scheme: A construction of second generation wavelets. SIAM J. Math. Anal., 29(2):511-546, 1997.
28. Chen P C, Lee S, Kuo CD. Delineation of T-wave in ECG by wavelet transform using multiscale differential operator. IEEE Trans Biomed Eng. 2006 July; 53(7):1429-33.
29. Chouakri S. A., et al. ECG signal smoothing based on combining wavelet denoising levels. Asian Journal of Information Technology. Vol 5, pp. 667-677. 2006.
30. Donoho, D. L., "Denoising by soft-thresholding," IEEE Trans. on Inf. Theory, 42 3, pp. 613-627, 1995.

Based upon the above discussion and illustrations, those skilled in the art will readily recognize that various modifications and changes may be made to the present invention without strictly following the exemplary embodiments and applications illustrated and described herein. For example, various thresholds as discussed herein may be used in an inverse sense, with embodiments described as involving a determination of a value exceeding the threshold can be implemented via values that fall below a threshold. In addition, the various manners in which to denoise signals, filter signals, combine or otherwise process signals as discussed in connection with certain embodiments, may also be implemented with other embodiments. Similarly, aspects discussed in connection with and/or shown in the figures may be implemented with other embodiments in other figures or otherwise discussed herein. Such modifications do not depart from the true spirit and scope of the present invention, including that set forth in the following claims.

What is claimed is:

1. An apparatus comprising:
  a circuit-based computer configured and arranged with executable instructions to
    identify a T-wave offset point within a first time window of an ECG signal, and
    provide the identified T-wave offset point as an output based upon a noise characteristic of the ECG signal in a second time window that includes at least a portion of the T-wave of the ECG signal.

2. The apparatus of claim 1, wherein the circuit-based computer is configured and arranged with the executable instructions to identify the T-wave offset point by
- identifying a location of a QRS complex in the ECG signal,
- identifying the first time window based upon a location of the QRS complex,
- computing a T-wave emphasis signal, and
- evaluating the emphasis signal within the first time window to identify the T-wave offset point as a first baseline point after a last significant peak or valley of the emphasis signal.

3. The apparatus of claim 2, wherein the circuit-based computer is configured and arranged with the executable instructions to compute the T-wave emphasis signal by:
- decomposing the ECG signal into subcomponents,
- identifying subcomponents in the first time window as either primarily associated with noise or primarily associated with the T-wave of the underlying ECG signal, and
- using at least one of the subcomponents primarily associated with the T-wave as the emphasis signal.

4. The apparatus of claim 1, further including a non-transitory electronic data storage medium that includes the instructions stored thereupon.

5. The apparatus of claim 1, wherein the second time window includes the identified T-wave offset point.

6. The apparatus of claim 1, wherein the second time window has a duration of about 30% of the duration of a nominal QT interval of the ECG signal, and extends beyond the T-wave offset point by about 10% of the nominal QT interval duration.

7. The apparatus of claim 1, wherein the second time window has a duration of about 50 msec and is centered on about the identified T-wave offset point.

8. The apparatus of claim 1, wherein the second time window extends from about the point of a largest deflection of the T-wave from an isoelectric line of the ECG signal to about the T-wave offset point.

9. The apparatus of claim 1, wherein the second time window includes a time period extending from about a QRS offset point in the ECG signal to about the T-wave offset point.

10. The apparatus of claim 1, wherein the second time window includes a time period extending the full duration of a cardiac cycle in the ECG signal.

11. The apparatus of claim 1, wherein the circuit-based computer is configured and arranged with the executable instructions to compute the noise characteristic by:
- decomposing the ECG signal into subcomponents,
- identifying said subcomponents in the second time window as either primarily associated with noise or primarily associated with the T-wave of the underlying ECG signal,
- computing a noise signal for the second time window by using at least one subcomponent not primarily associated with the T-wave, and
- computing said noise characteristic based upon at least one of: energy of the noise signal, standard deviation of the noise signal, zero crossing density of the noise signal, a metric of noise amplitude computed using an envelope of the noise signal, and a metric of energy of the ECG signal relative to energy of the noise signal.

12. The apparatus of claim 11, wherein the circuit-based computer is configured and arranged with the executable instructions to
- compute a metric of energy of the ECG signal using at least one of the subcomponents within the second time window that are primarily associated with the T-wave.

13. The apparatus of claim 1, wherein the circuit-based computer is configured and arranged with the executable instructions to compute the noise characteristic by:
- computing a denoised signal for the second time window using at least one of a band-pass filter, wavelet thresholding, and an adaptive filter that passes primarily T-wave energy,
- capturing a residual of the step of computing the denoised signal as a noise signal for the second time window, and
- computing said noise characteristic based upon at least one of: energy of the noise signal, standard deviation of the noise signal, zero crossing density of the noise signal, a metric of noise amplitude computed using an envelope of the noise signal, and a metric of energy of the denoised signal relative to energy of the noise signal.

14. The apparatus of claim 1, wherein the circuit-based computer is configured and arranged with the executable instructions to provide the identified T-wave offset point as an output based upon a noise characteristic of the ECG signal in the second time window by comparing the noise characteristic to a threshold and providing the identified T-wave offset point based upon the comparison.

15. The apparatus of claim 1, wherein the circuit-based computer is configured and arranged with the executable instructions to provide the identified T-wave offset point based upon a presence, in a cardiac cycle within the ECG, of at least one of: atrial fibrillation, QT dispersion in a multi-lead ECG exceeding a threshold, T-wave morphology complexity exceeding a predefined threshold, ventricular ectopy, a QT interval measurement that falls outside of a user-defined physiologic outlier value or a statistical outlier value.

16. The apparatus of claim 1, wherein the circuit-based computer is configured and arranged with the executable instructions to assemble a time series of provided QT interval values for analysis of variability using the provided identified T-wave offset point.

17. An apparatus for providing a repolarization signal for a cardiac cycle of an ECG signal, the apparatus comprising:
- a circuit-based computer configured and arranged with executable instructions to
  - identify the location of a QRS complex in the cardiac cycle;
  - identify T-wave onset and offset points based on the identified location of the QRS complex;
  - define the start and end of the repolarization signal for the cardiac cycle, based respectively upon the T-wave onset and offset points;
  - determine a noise characteristic of the ECG signal in a time window spanning from about the start to about the end of the repolarization signal, and
  - providing the repolarization signal as an output, based upon the determined noise characteristic.

18. The apparatus of claim 17, wherein the circuit-based computer is configured and arranged with the executable instructions to determine the noise characteristic by:
- decomposing the ECG signal into subcomponents,
- identifying ones of said subcomponents of the ECG signal within the time window as primarily associated with the T-wave of the underlying ECG signal,
- computing a noise signal for the time window using at least one of the subcomponents not primarily associated with the T-wave, and
- computing said noise characteristic based upon at least one of: energy of the noise signal, standard deviation of the noise signal, zero crossing density of the noise signal, a metric of noise amplitude computed using an envelope of the noise signal, and a metric of energy of the ECG signal relative to energy of the noise signal.

19. The apparatus of claim 18, wherein the circuit-based computer is configured and arranged with the executable instructions to
compute a metric of energy of the ECG signal using at least one of the subcomponents within the second time window that is primarily associated with the T-wave.

20. The apparatus of claim 17, wherein the circuit-based computer is configured and arranged with the executable instructions to compute an output repolarization signal by
decomposing the ECG signal into subcomponents,
identifying ones of said subcomponents of the ECG signal within the time window as primarily associated with the T-wave of the underlying ECG signal, and
computing said output repolarization signal by combining at least two of the subcomponents that are primarily associated with the T-wave.

21. The apparatus of claim 17, wherein the circuit-based computer is configured and arranged with the executable instructions to compute the noise characteristic by:
computing a denoised signal for the time window using at least one of a band-pass filter, wavelet thresholding, and an adaptive filter that passes primarily T-wave energy,
computing a noise signal for the time window using a residual of the step of computing the denoised signal, and
computing said noise characteristic based upon at least one of: energy of the noise signal, standard deviation of the noise signal, zero crossing density of the noise signal, a metric of noise amplitude computed using an envelope of the noise signal, and a metric of energy of the denoised signal relative to energy of the noise signal.

22. The apparatus of claim 17, wherein the circuit-based computer is configured and arranged with the executable instructions to compare the noise characteristic to a threshold and provide the repolarization signal as an output based upon the comparison.

23. The apparatus of claim 17, wherein the circuit-based computer is configured and arranged with the executable instructions to provide a repolarization signal as an output based upon the determined noise characteristic and the presence in the cardiac cycle of at least one of: atrial fibrillation in the ECG signal, a degree of QT dispersion exceeding a threshold when the ECG signal is a multi-lead signal, T-wave morphology complexity of the ECG signal exceeding a threshold, ventricular ectopy, and a QT interval measurement that falls outside of a user-defined physiologic outlier value or a statistical outlier value.

24. The apparatus of claim 17, wherein the circuit-based computer is configured and arranged with the executable instructions to append the provided repolarization signal to a matrix of repolarization signals in which a dimension of the matrix corresponds to the number of cardiac cycles of the ECG signal.

25. An apparatus for providing a time series of beat-to-beat QT interval values from a digitized ECG signal of an ambulatory subject, the apparatus comprising:
a circuit-based computer configured and arranged with executable instructions to
identify the location of a QRS complex and a Q-wave onset point of a cardiac cycle of the ECG signal;
determine a first time window of the cardiac cycle in which to search for a T-wave offset point for a T-wave in the cardiac cycle, based upon one of the identified location of the QRS complex and the identified location of the Q-wave onset point;
identify the T-wave offset point within the first time window;
compute a QT interval value using the identified Q-wave onset point of the QRS complex and the identified T-wave offset point, and
provide the QT interval value in a time series of beat-to-beat QT interval values, based upon a noise characteristic of the digitized ECG signal in a second time window that includes at least a portion of the T-wave.

26. The apparatus of claim 25, wherein the circuit-based computer is configured and arranged with the executable instructions to, prior to identifying the T-wave offset point, suppress energy in a portion of the digitized ECG signal that is not primarily associated with T-wave energy in the first time window, using at least one of MDSP denoising, wavelet threshold denoising, band-pass filtering, and adaptive filtering.

27. The apparatus of claim 25, wherein the circuit-based computer is configured and arranged with the executable instructions to compute the noise characteristic by:
decomposing the digitized ECG signal into subcomponents,
identifying said subcomponents as primarily associated with either noise or a T-wave of an underlying ECG signal,
computing a noise signal by combining the subcomponents within the second time window that are primarily associated with noise,
computing a denoised signal by combining the subcomponents within the second time window that are primarily associated with the T-wave of the underlying ECG signal, and
computing said noise characteristic based upon at least one of: energy of the noise signal, standard deviation of the noise signal, zero crossing density of the noise signal, a metric of noise amplitude based upon an envelope of the noise signal, and a metric of energy of the denoised signal relative to energy of the noise signal.

28. The apparatus of claim 27, wherein the metric of energy of the denoised signal relative to energy of the noise signal is a signal-to-noise ratio.

29. The apparatus of claim 25, wherein the circuit-based computer is configured and arranged with the executable instructions to compute the noise characteristic by:
computing a denoised signal for the second time window using at least one of a band-pass filter, wavelet thresholding, and an adaptive filter, and computing a noise signal as a difference between the digitized ECG signal and the denoised signal, and
computing said noise characteristic based upon at least one of: energy of the noise signal, standard deviation of the noise signal, zero crossing density of the noise signal, a metric of noise amplitude computed using an envelope of the noise signal, and a metric of energy of the denoised signal relative to energy of the noise signal.

30. The apparatus of claim 25, wherein the circuit-based computer is configured and arranged with the executable instructions to provide the QT interval value in the time series of beat-to-beat QT interval values based upon a comparison of the noise characteristic to a threshold value.

31. The apparatus of claim 25, wherein the circuit-based computer is configured and arranged with the executable instructions to provide the QT interval value in the time series of beat-to-beat QT interval values based upon the noise characteristic and the presence, in the cardiac cycle, of at least one of: atrial fibrillation, ventricular ectopy, QT dispersion in a multi-lead ECG exceeding a threshold, T-wave morphology complexity exceeding a predefined threshold, ventricular ectopy, a QT interval measurement that falls outside of a user-defined physiologic outlier value or a statistical outlier value.

32. The apparatus of claim 25, wherein the circuit-based computer is configured and arranged with the executable instructions to
- repeat the steps to compute a plurality of the QT interval values, and
- provide ones of the QT interval values in the time series of beat-to-beat QT interval values based upon a comparison of a noise characteristic of a corresponding ECG signal in the second window to a predefined threshold.

33. The apparatus of claim 25, wherein the circuit-based computer is configured and arranged with the executable instructions to compute a marker of arrhythmogenic risk by computing, using the beat-to-beat QT interval values, at least one of:
- QT interval alternans,
- short-term variability of QT intervals,
- long-term variability of QT intervals,
- root mean square, standard deviation of QT interval successive differences, and
- multiscale entropy.

34. The apparatus of claim 25, wherein the circuit-based computer is configured and arranged with the executable instructions to provide the time series of beat-to-beat QT intervals consisting of QT interval values having error due to noise that is less than 2.5% of a mean QT interval of the ECG signal.

35. A computer program product, comprising:
- a non-transitory computer readable medium storing executable program instructions, which when executed by a computing apparatus, cause the computing apparatus system to perform a method comprising:
    - identifying a T-wave offset point within a first time window of an ECG signal, and
    - providing the identified T-wave offset point as an output based upon a noise characteristic of the ECG signal in a second time window that includes at least a portion of the T-wave of the ECG signal.

36. The computer program product of claim 35, wherein the non-transitory computer readable medium stores executable program instructions that, which when executed by the computing apparatus, causes the computing apparatus system to
- identify the location of a QRS complex in the ECG signal, and determine the first time window based upon the identified location of the QRS complex.

* * * * *

UNITED STATES PATENT AND TRADEMARK OFFICE
CERTIFICATE OF CORRECTION

| | | |
|---|---|---|
| PATENT NO. | : 9,050,007 B1 | Page 1 of 1 |
| APPLICATION NO. | : 13/872774 | |
| DATED | : June 9, 2015 | |
| INVENTOR(S) | : Brockway et al. | |

It is certified that error appears in the above-identified patent and that said Letters Patent is hereby corrected as shown below:

In the Specification

Column 1, Line 2, insert the following after the title:
--STATEMENT REGARDING FEDERALLY SPONSORED RESEARCH AND DEVELOPMENT
This invention was made with government support under grant numbers R44DA011815 and R43HL110739 awarded by the National Institutes of Health. The government has certain rights in the invention.--

Signed and Sealed this
Eleventh Day of March, 2025

Coke Morgan Stewart
*Acting Director of the United States Patent and Trademark Office*